United States Patent [19]

Dervan et al.

[11] Patent Number: 4,665,184

[45] Date of Patent: May 12, 1987

[54] BIFUNCTIONAL MOLECULES HAVING A DNA INTERCALATOR OR DNA GROOVE BINDER LINKED TO ETHYLENE DIAMINE TETRAACETIC ACID

[75] Inventors: Peter B. Dervan, South Pasadena; Robert P. Hertzberg, Pasadena, both of Calif.

[73] Assignee: California Institute of Technology, Pasadena, Calif.

[21] Appl. No.: 860,604

[22] Filed: May 7, 1986

Related U.S. Application Data

[63] Continuation of Ser. No. 540,914, Oct. 12, 1983, abandoned, which is a continuation-in-part of Ser. No. 338,332, Jan. 11, 1982, abandoned.

[51] Int. Cl.$^4$ .......................................... C07D 221/12
[52] U.S. Cl. .................................. 546/109; 260/115; 548/403
[58] Field of Search ........................................ 546/109

[56] References Cited

U.S. PATENT DOCUMENTS 2,267,988  12/1941  Morgan et al. ...................... 546/109
4,335,226   6/1982  Müller et al. ...................... 546/109

Primary Examiner—Glennon H. Hollrah
Assistant Examiner—James H. Turnipseed
Attorney, Agent, or Firm—Joseph E. Mueth

[57] ABSTRACT

Novel bifunctional molecules having a DNA intercalator or DNA groove binder linked to ethylene diamine tetraacetic acid such as compounds having the formula:

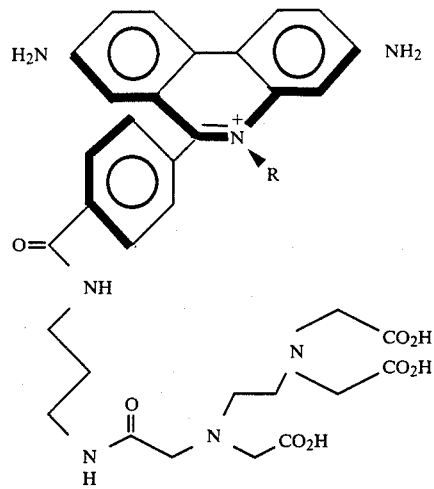

wherein R is methyl or ethyl.

Also, the method of cleaving DNA by contact with one of the above-identified molecules in the presence of ferrous ion and oxygen.

The process of preparing said molecules by the reaction of P-carboxy methidium halide, p-carboxy ethidium halide, or other DNA intercalator or DNA groove binder with 1-3-diaminopropane followed by condensation with ethylenediamine tetraacetic acid.

Distamycin-EDTA.Fe(II)(DE.FE(II)) contains EDTA attached to the amino terminus of the groove binder tripeptide (tris-N-methylpyrrolecarboxamide). DE.-Fe(II) cleaves DNA contiguous to a five base pair A+T rich sequence. This is a novel and unique molecule and superior in sequence specificity to the naturally occurring antitumor compound used in man, bleomycin which cleaves DNA at a two base pair recognition site. EDTA-distamycin-Fe(II)(ED.Fe(III)) contains EDTA attached to the carboxy terminus of the groove binder tripeptide, tris-N-methylpyrrolecarboxamide. ED.-Fe(II) cleaves DNA contiguous to a five base pair A+T rich sequence. Penta-N-methylpyrrolecarboxamide-EDTA.Fe(II)(P5E.Fe(II)) cleaves DNA on opposite strand at the six base pair recognition level in a catalytic reaction. This is the first designed synthetic molecule that approximates the double strand sequence specific cleavage of DNA(4-6 bp recognition level) by the natural substance restriction enzymes, tools which make possible recombinant DNA manipulations. P5E.-Fe(II) cuts DNA at sequences not available by the naturally occurring restriction enzymes.

The dimers, bis(EDTA-distamycin.Fe(II) and EDTA-bisdistamycin.Fe(II) which double strand cleave DNA at the eight base pair recognition level (A+T rich).

3 Claims, No Drawings

BIFUNCTIONAL MOLECULES HAVING A DNA INTERCALATOR OR DNA GROOVE BINDER LINKED TO ETHYLENE DIAMINE TETRAACETIC ACID

This application is a continuation of application Ser. No. 540,914, filed Oct. 12, 1983, which was a continuation-in-part of Ser. No. 338,332 filed 1/11/82, both now abandoned.

BACKGROUND OF THE INVENTION

Metal ions have been implicated as cofactors in the strand scission of DNA for a number of antitumor antibiotics. Bleomycin, a glycopeptide antibiotic, is known to bind to and cleave DNA in a reaction that depends on the presence of ferrous ion and molecular oxygen, "Bleomycin: Chemical, Biochemical and and Biological Aspects"; Hecht, S. M., Ed.; Springer Verlag: New York, 1979; Sausville, E. A.; Peisach, J.; Horwitz, S. B. "Biochemistry" 1978, 17, 2740. Burger, R. M.; Peisach, J; Horwitz, S. B. "Life Sciences" 1981, 28, 715; and Lown, J. W.; Sim, S. F. "Biochem. Biophys. Res. Comm." 1977, 77, 1150. The antitumor agent streptonigrin is also capable of causing single strand breaks in DNA using oxygen and cuprous ion, Cone, R., Hasan, S. K.: Lown, J. W.; Morgan, A. R. "Can. J. Biochem." 1976, 54, 219. Recently, the 1-10 phenanthroline-cuprous complex has been shown to cleave DNA in the presence of oxygen, Sigman, D. S.; Graham, D. R.: D'Aurora, V.; Stern, A. M. "J. Biol. Chem." 1979, 254, 12269; Graham, D. R.: Marshall, L. E.; Reich, K. A.: Sigman, D. S. "J. Amer. Chem. Soc." 1980, 102, 5419: Marshall, L. E.; Graham, D. R.; Reich, K. A.; Sigman, D. S. "Biochemistry" 1981, 20, 244: and Que, B. G.; Downey, K. M.; So., A. G. "Biochemistry" 1980, 19, 5987, These examples involve the concept of using a DNA binding molecule to deliver a metal ion to the site of the DNA helix where activation of molecular oxygen results in cleavage of the DNA.

According to the present invention, we have discovered a class of new bifunctional molecules containing a DNA intercalator or DNA groove binder molecule linked to ethylene diamine tetraacetic acid. An example of our invention is the synthesis of a simple bifunctional molecule, methidium-propyl-EDTA (MPE) which contains the DNA intercalator, methidium or ethidium covalently bound by a short hydrocarbon tether to the metal chelator, ethylene diamine tetraacetic acid. In the presence of ferrous ion and oxygen, MPE has been discovered to efficiently produce single strand breaks and some double strand breaks in double helical DNA with lower sequence specificity than the naturally occurring enzyme, DNase I. The efficient and low sequence specific DNA cleaving ability of MP.Fe(II) afford a new synthetic tool for DNA and RNA manipulations superior to the naturally occurring enzyme DNase I.

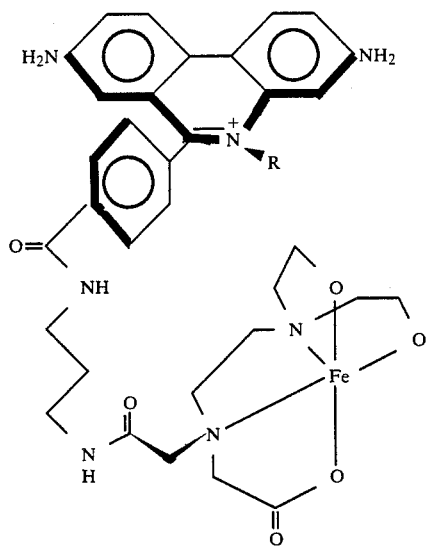

In the above formula R is methyl or ethyl.

The novel compounds distamycin EDTA.Fe(II), EDTA-distamycin.Fe(II), penta-N-methylpyrrolecarboxamide-EDTA.Fe(II), bis(EDTA-distamycin).Fe(II) and EDTA(bisdistamycin).Fe(II) are effective as sequence specific DNA cleavers.

SUMMARY OF THE INVENTION

Briefly the present invention comprises novel bifunctional molecules having a DNA intercalator or DNA groove binder linked to ethylene diamine tetraacetic acid (EDTA) such as compounds having the formula:

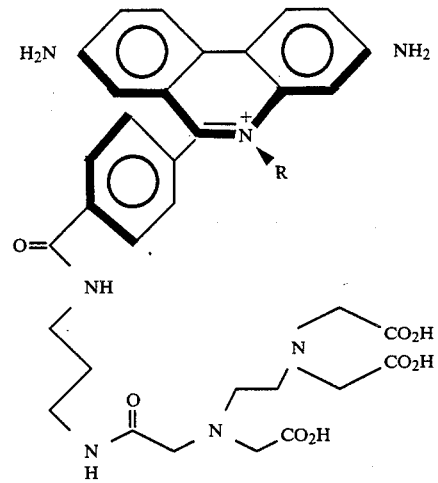

wherein R is methyl or ethyl; distamycin EDTA: EDTA distamycin: penta-N-methylpyrrolecarboxamide EDTA; bis(EDTA distamycin) and EDTA-(bisdistamycin).

The present invention further includes the preparation of the compounds of the structural formula, known as methidium (or ethidium)-propyl-ethylenediamine tetraacetic acid by the reaction of p-carboxy methidium halide or p-carboxy ethidium halide with 1,3-diaminopropane followed by condensation with ethylenediamine tetraacetic acid. DNA intercalators are a known class of compounds that bind noncovalently to duplex DNA and are characterized by a flat molecule which inserts between base pairs of the double helix of DNA. Examples include p-carboxy methidium, p-carboxy ethidium, acridine and ellipticine.

DNA groove binders are also a recognized group of DNA binders and are characterized by their ability to fit snuggly within the grooves of the DNA helix. Examples of DNA groove binders are netropsin, distamycin and actinomycin.

This invention also comprehends the method of cleaving DNA by contact with any one of the above-identified molecules linked to EDTA in the presence of ferrous ion and oxygen.

It is an object of this invention to provide a novel class of chemical compounds.

Still another object of this invention is the novel process of preparing certain new chemical compounds.

It is also an object of this invention to provide a novel means for cleaving the DNA molecule.

These and other objects and advantages of the invention will be apparent from the detailed description which follows.

DESCRIPTION OF THE PREFERRED EMBODIMENTS OF THE INVENTION

The following Examples are presented solely to illustrate the invention.

The method of preparation of one category of the new compounds is shown by the following reaction equation:

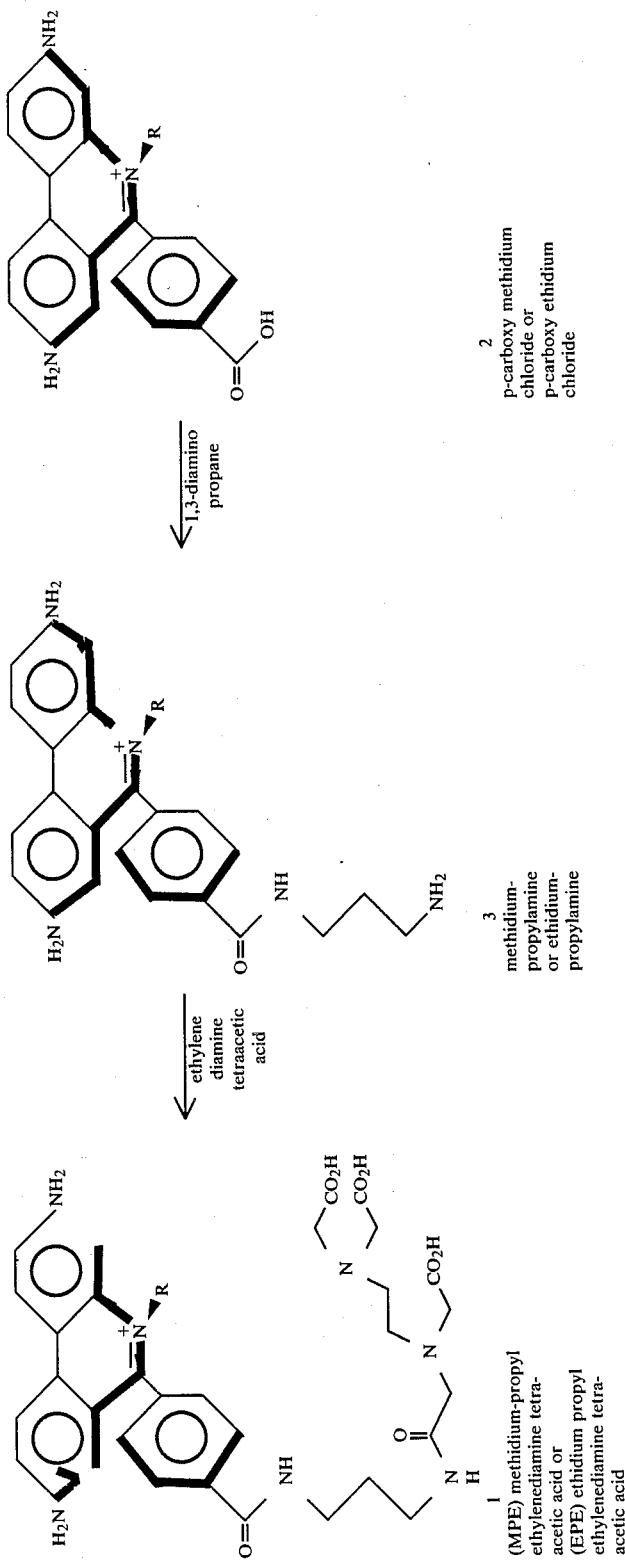

EXAMPLE I

The acylimidazole ester of p-carboxy methidium chloride (obtained from May—Baker), was allowed to react with an excess of 1,3-diaminopropane in dimethyl sulfoxide (DMSO) at 25° affording a maroon solid product, methidiumpropylamine (3). Condensation of 3 with excess EDTA in dry DMF/120° yielded methidium-propyl-EDTA (MPE), in an overall yield of 59% after chromatography on silica gel 60 (230–400 mesh ASTM). MPE was rendered metal-free by treatment of an acidic aqueous solution with Na$_2$EDTA followed by purification of Amberlite XAD-2 polystyrene resin.*

*MPE was ≧99% pure by HPLC in two solvent systems (ALTEX Ultrasphere ODS; 86:14 H$_2$O:CH$_3$CN, retention time 8.4 minutes and 70:30 H$_2$O:MeOH, retention time 19.2 minutes). The nmr and ir spectra data were consistent with the assigned structure. MPE was isolated from methanol/water as the hexahydrate. Anal. Calcd. for C$_{34}$H$_{51}$N$_7$O$_{14}$:C, 52.23; H, 6.57; N, 12.54. Found: C, 52.48; H, 6.12; N, 12.50.

EXAMPLE II

In the following, the cleavage of DNA was followed by monitoring the conversion of supercoiled (Form I) pBR-322 plasmid DNA, $10^{-5}$ M in base pairs (bp), to open circular and linear forms (Forms II and III, respectively. The introduction of one single strand break converts Form I to Form II. The simple chelate of ethylene diamine tetraacetic acid with ferrous ion, EDTA.Fe(II) at $>10^{-4}$ M concentrations will cleave plasmid DNA, however at concentrations $\leq 10^{-4}$ M little or no cleavage takes place. The addition of intercalator ethidium bromide (EB) to Fe(II) or EDTA.Fe(II) does not promote the cleavage reaction. Thus, we believe it is notable that MPE.Fe(II) at two orders of magnitude lower concentration ($10^{-6}$ M) cleaves plasmid DNA (Table I). MPE alone or MPE.Fe(III) is inactive at these concentrations. In the presence of dithiothreitol (DTT), MPE.Fe(II) at $10^{-8}$ M concentration cleaves plasmid DNA with even greater efficiencies, comparable to efficiencies found with bleomycin (Table II). Presumably, DTT acts as a reducing agent and regenerates Fe(II) from Fe(III) to produce a continuous source of active metal ion.

TABLE I

Cleavage of pBR-322 Plasmid[a]

| Reagent | Concentration (M) | Percent Form I | II | III | s[b] |
|---|---|---|---|---|---|
| Fe(II) | $10^{-4}$ | 92 | 8 | 0 | 0.08 |
| EDTA.Fe(II)[c] | $10^{-4}$ | 94 | 6 | 0 | 0.06 |
| EDTA.Fe(II)[c] | $5 \times 10^{-4}$ | 38 | 62 | 0 | 0.97 |
| MPE.Fe(II) | $10^{-6}$ | 72 | 28 | 0 | 0.33 |
| MPE.Fe(II) | $5 \times 10^{-6}$ | 40 | 60 | 0 | 0.92 |
| Bleomycin.Fe(II) | $10^{-7}$ | 65 | 29 | 6 | |
| Bleomycin.Fe(II) | $10^{-6}$ | 0 | 49 | 51 | |

[a]Form I pBR-322($10^{-5}$ M bp), reagent and buffer (40 mM Tris-HCl, 5 mM NaOAC, pH 7.8) were allowed to react at 37° for 60 min. Forms I, II, and III were analyzed with agarose gel electrophoresis and quantitated by ethidium bromide staining and densitometry.
[b]Calculated average number of strand scissions per DNA molecule. These values cannot be calculated for bleomycin because of a nonrandom accumulation of single-strand breaks.
[c]Values are the same for EDTA.Fe(II) in the presence of $10^{-5}$ M EB.

TABLE II

Cleavage of pBR-322 Plasmid in the Presence of DTT.[a]

| Reagent | Concentration (M) | Percent Form I | II | III | s[b] |
|---|---|---|---|---|---|
| MPE.Fe(II) | $10^{-8}$ | 82 | 18 | 0 | 0.20 |
| | $10^{-7}$ | 43 | 57 | 0 | 0.84 |
| | $10^{-6}$ | 0 | 85 | 15 | 9.2 |
| Bleomycin.Fe(II) | $10^{-8}$ | 67 | 29 | 4 | |
| | $10^{-7}$ | 0 | 79 | 21 | |
| | $10^{-6}$ | 0 | 54 | 46 | |
| Fe(II) | $10^{-6}$ | 90 | 10 | 0 | 0.11 |

[a]All reactions contain 1 mM DTT. Reaction conditions and analyses are as in Table I.

Inhibition studies reveal the following (Table III). Addition of Fe(II) to MPE in the presence of strong iron chelators such as desferrioxamine (Des) or EDTA shows no DNA cleavage. Addition of Fe(II) to MPE.Ni(II) or MPE.Zn(II) shows no DNA cleavage. Ni(II) and Zn(II) are known to form stable complexes with EDTA, and presumably compete with Fe(II) for the chelation site on MPE.

TABLE III

Inhibition Studies[a]

| Inhibitor | Concentration (M) | Percent Form I | II | III | S |
|---|---|---|---|---|---|
| none | | 38 | 62 | 0 | 0.97 |
| EDTA | $10^{-2}$ | 86 | 14 | 0 | 0.15 |
| EDTA | $5 \times 10^{-2}$ | 94 | 6 | 0 | 0.06 |
| Des | $10^{-2}$ | 97 | 3 | 0 | 0.03 |
| Des | $5 \times 10^{-2}$ | 100 | 0 | 0 | 0.0 |
| Ni(II) | $10^{-4}$ | 98 | 2 | 0 | 0.02 |
| Zn(II) | $10^{-4}$ | 88 | 12 | 0 | 0.13 |
| Superoxide dismutase | 100 μg/ml | 81 | 19 | 0 | 0.21 |
| Catalase | 100 μg/ml | 96 | 4 | 0 | 0.04 |

[a]pBR-322 plasmid DNA ($10^{-5}$ M bp), MPE ($10^{-5}$ M), and inhibitor were combined in buffer and then Fe(II) ($10^{-5}$ M) was added. Analysis was carried out as in Table I.

The reacations of MPE.Fe(II) and plasmid DNA with and without DTT were repeated in the absence of oxygen and no strand scission was observed. The nature of the activated oxygen species in the MPE.Fe(II) reaction which cleaves the DNA is not yet known. While not bound by any theory, two classes of intermediates that might be considered as the ultimate DNA-cleaving species are free oxygen radicals or an iron-bound oxygen species, Groves, J. T. "Metal Ion Activation of Dioxygen"; Spiro, T. C., Ed.; John Wiley and Sons, New York, 1980; p. 146. Superoxide ion (O$_2^-$) has been shown to be involved in the single-strand scission of DNA in the presence of trace metal ions, Lesko, S. A.; Lorentzen, R. J.; Ts'l, P.O.P. "Biochemistry" 1980, 19, 3023. Superoxide has also been implicated as an intermediate in the reaction mechanisms of bleomycin, streptonigrin, and Cu-phenanthroline. In these systems, hydroxyl radicals are suggested to be at least one ultimate species which degrades DNA. Hydrogen peroxide has been implicated as an intermediate in the hydroxyl radical generation by known Fenton-type chemistry.

The enzyme superoxide dismutase (SOD) converts superoxide to hydrogen peroxide and oxygen, Malstrom, B. G.; Andreasson, L. E.; Reinhammar, B. in "The Enzymes", Vol. XII; Boyer, P. D., Ed. Academic Press: New York, 1975, p. 533, thus depleting the system of "free" superoxide. The observation that SOD inhibits the MPE.Fe(II) cleavage of DNA indicates the importance of O$_2^-$. Catalase, which converts hydrogen peroxide to water and oxygen, Schonbaum, G. R.; Chance, B. in "The Enzymes"; Vol. XIII; Boyer, P. D., Ed.; Academic Press: New York, 1976; p. 363, also inhibits the MPE.Fe(II) DNA cleavage reaction indicating the apparent importance of "free" hydrogen peroxide as an intermediate in strand scission (Table III).

With regard to iron-bound oxygen as the ultimate DNA cleaving species, it has been found that direct oxidation of MPE.Fe(III) ($10^{-5}$ M) with iodosylbenzene (Ph10) ($10^{-5}$ M) enhances cleavage of plasmid DNA. Whether this involves a ferryl species MPE will be the subject of future work. Controls show that Ph10 and EDTA.Fe(III) ($10^{-5}$ M) or Ph10 ($10^{-5}$ M) alone do not cleave DNA.

In summary, MPE cleaves plasmid DNA in a reaction that is dependent on Fe(II) and $O_2$ at concentrations of two orders of magnitude lower than EDTA.Fe(II). In the presence of DTT concentrations of MPE.Fe(II) as low as $10^{-8}$ M cleave DNA comparable to efficiencies found with the antibiotic bleomycin. It appears that an interpretation consistent with the data suggests that the intercalator portion of MPE "delivers" the iron/oxygen chemistry to the DNA helix.

The present invention is useful in the efficient cleavage of plasmid DNA. The cleaved DNA is now widely used in a variety of processes and techniques familiar to those skilled in the art. It also appears that like bleomycin, MPE and EPE may be useful in cancer chemotherapy.

The attachment of EDTA.Fe(II) to distamycin changes the sequence specific DNA binding antibiotic into a sequence specific DNA cleaving molecule. This invention includes the snthesis of EDTA-distamycin(ED) which has the metal chelator, EDTA, tethered to the carboxy terminus of the N-methylpyrrole tripeptide moiety of the antibiotic, distamycin. EDTA-distamycin.Fe(II) (ED.Fe(II)) at $10^{-6}$ M concentration efficiently cleaves pBR322 DNA ($10^{-5}$ M in base pairs) in the presence of oxygen and dithiothreitol (DTT). Using Maxam-Gilbert sequencing gel analyses, it has been found that ED.Fe(II) affords DNA cleavage patterns of unequal intensity covering two to four contiguous base pairs adjacent to a four base pair site consisting of adenines (A) and thymines (T). The multiple cleavages at each site might be evidence for a diffusible oxidizing species, perhaps hydroxyl radical. The unequal intensity of cleavage on each side of the A+T site permit assignment of major and minor orientations of the tripeptide binding unit. A comparison of the cleavage specificity of ED.Fe(II) with distamycin-EDTA.Fe(II), (DE.Fe(II)) which has EDTA.Fe(II) attached to the amino terminus of the N-methylpyrrole tripeptide, shows DNA cleavage patterns at the same sites but with intensities of opposite polarity. Maxam-Bilbert sequencing gel analysis of the DNA cleavage patterns by ED.Fe(II) and DE.Fe(II) on both DNA strands of a 381 base pair restriction fragment reveals asymmetric DNA cleavage patterns. Cleavage is shifted to the 3' side of each DNA strand. A model consistent with this cleavage pattern indicates one preferred binding site for ED.Fe(II) and DE.FE(II) is 3'-TTTAA-5' with the "amino end" of the tripeptide oriented to the 3' end of the thymine rich strand.

This "DNA affinity cleavage" method which consists of attaching cleaving functions such as a metal and chelator capable of redox chemistry to DNA binding molecules followed by DNA cleavage pattern analyses from Maxam-Gilbert sequencing gels may be a useful direct method for determining the binding site and orientation of small molecules on DNA. This strategy changes the function of sequence specific DNA binding molecules affording a new class of sequence specific DNA cleaving molecules that may form the primitive basis for the design and construction of "artificial restriction enzymes" with defined target sequences and binding site sizes.

Many small molecules important in antibiotic, antiviral, and antitumor chemotherapy bind to double helical DNA. Our knowledge of the base sequence preferences of most DNA binding drugs is somewhat limited due to the restricted information obtained by spectrophotometric analyses of the overall binding affinity on synthetic homopolymer and copolymer DNAs. A smaller class of DNA binding molecules are bifunctional in nature, combining a chemically reactive moiety with a DNA binding unit. One such molecule is the naturally occurring antitumor, antibiotic bleomycin which cleaves DNA in a reaction that depends on Fe(II) and oxygen. "Bleomycin: Chemical, Biochemical and Biological Aspects"; S. M. Hecht, Ed.; Springer-Verlag: New York, 1979. R. M. Burger, J. Peisach, S. B. Horowitz, Life Sci., 28, 715–727 (1981). The DNA cleaving function of bleomycin in combination with Maxam-Gilbert sequencing gel analyses affords precise information on the sequence specificity of bleomycin binding. From DNA cleavage patterns obtained from reaction of bleomycin.Fe(II) with end labeled DNA restriction fragments it is known that bleomycin cleaves DNA at the pyrimidine of a two base pair 5'-GT-3' or 5'-GC-3' recognition site. M. Takeshita, L. Kappen, A. P. Grollman, M. Eisenberg, I. Goldberg, Biochemistry, 20, 7599–7606 (1981). M. Takeshita, Ap. P. Grollman, E. Ohtusbo, H. Ohtsubo, Proc. Natl. Acad. Sci. USA, 75, 5983–5987 (1978) A. D. D'Andrea, W. A. Haseltine, Proc. Natl. Acad. Sci USA, 75, 3608–3612 (1978). The structure of the bleomycin.Fe(II):DNA complex is not known. Unlike bleomycin.Fe(II), MPE.Fe(II) cleaves DNA in a non-sequence specific manner consistent with spectrophotometric binding studies that indicate that methidium has no overall base composition specificity. (a) M. J. Waring, J. Mol. Biol., 13, 269–282 (1965). J. B. LePacq, C. Paoletti, J. Mol. Biol., 27, 87–106 (1967). (b) W. Muller, D. M. Crothers, Eur. J. Biochim., 54, 267–277 (1975). (c) J. L. Bresloff, D. M. Crothers, Biochemistry, 20, 3457–3552 (1981). The lack of sequence specificity in the DNA cleavage reaction suggests that MPE.Fe(II) mimics the function of DNase I, an enzyme which cleaves double helical DNA in a relatively non-sequence specific manner. (a) A. Bernardi, C. Gaqillard, G. B. Bernardi, Eur. J. Biochim., 52, 451–457 (1975). (b) A. Bernardi, S. D. Ehrlich, J. Thiery, Nature, 246, 36–40 (1973). Because MPE.Fe(II) cleaves DNA with lower sequence specificity than DNase I, MPE.Fe(II) partial cleavage of drug protected DNA restriction fragments in combination with Maxam-Gilbert sequencing gel analysis of the DNA cleavage inhibition patterns provides a rapid and direct method called "MPE.Fe(II) footprinting" for determining the locations and size of the binding sites of small molecules on the native DNA template.

We undertood the attachment of EDTA to sequence specific DNA binding molecules. We intend to change the "function" of sequence specific DNA binding molecules to sequence specific DNA cleaving molecules. The antibiotic distamycin is a tripeptide containing three N-methylpyrrole carboxamides which binds in the minor groove of double helical DNA with a strong preference for adenine and thymine rich regions. (a) K. E. Reinert, J. Mol. Biol., 72, 592 (1972). (b) G. Luck, Ch. Zimmer, K. E. Reinert, F. Arcamore, Nucl. Acids Res.

4, 2655 (1977). (c) B. Nosikov, B. Jain, *Nucl. Acids Res.*, 4, 2263 (1977). (d) For reviews see Ch. Zimmer, "Progress in Nucleic Acids Research and Molecular Biology", N. E. Cohn, Ed., Academic Press, New York, 1975, vol. XV, p. 285. (e) E. F. Gale, et al in "The Molecular Basis of Antibiotic Action", Wiley-Interscience, New York, 1981, p. 345. The sequence specificity of distamycin binding presumably results from hydrogen bonding between the amide NHs of the antibiotic and the O(2) of thymines and N(3) of adenines. (a) G. Luck, M. Treibel, M. Waring, Ch. Zimmer, *Nucl. Acids Res.*, 1, 5039 (1974). (b) A. S. Zasedatelev, A. L. Zhuze, Ch. Zimmer, S. L. Grokhovsky, V. G. Gursky, B. P. Gottikh, *Dokl. Acad. Nauk. SSSR*, 231,1006 (1976). (c) A. S. Krylov, S. L. Grokkhovsky, A. S. Zasedatelev, A. L. Zhuze, G. V. Gursky, B. P. Gottikh, *Nucl. Acids. Res.* 6, 289 (1979). We chose the N-methylpyrrole tripeptide as the sequence specific DNA binding unit for the subsequent attachment of EDTA.

It has been found that DE.Fe(II) in the presence of $O_2$ and DTT efficiently cleaves DNA. Importantly, DE.Fe(II) cleaves DNA restriction fragments at highly localized sites fewer in number than bleomycin.Fe(II). The fewer number of cleavage sites can be explained by larger binding site size requirements for DE.Fe(II) compared to that of bleomycin.Fe(II) whose binding site is known to be two base pairs. Initial studies revealed that DE.Fe(II) caused several DNA strand scissions of unequal intensity clustered on each side of a binding region composed of five A+T bases.

Herein below, we describe the synthesis and study of a new sequence specific DNA cleaving molecule, EDTA-distamycin(ED), which has the EDTA attached to the carboxy terminus of the tripeptide unit. We compare the relative cleavage efficiencies and base sequence specificities of ED.Fe(II) and DE.Fe(II) A comparison of the DNA cleavage patterns produced by DE.Fe(II) and ED.Fe(II) on of several restriction fragments affords new information on the binding sites and the preferred orientation on DNA of the tripeptide unit, and by extension, distamycin on DNA. Thus the EDTA attachment strategy leads to a class of "DNA affinity cleaving molecules" which allow binding sites of small molecules on heterogeneous DNA to be directly determined. The synthetic methodology used for the construction of DE and ED should be useful for future synthetic work on sequence specific DNA cleaving molecules.

EXAMPLE III

Synthesis of Distamycin EDTA

Nitro Acid 5

The nitro acid 5 was prepared according to the procedure of Bailer, M. Bailer, B. Yagen, R. Mechoulam, *Tetrahedron*, 34, 2389 (1978), on ten times the described scale with the following modifications. N-methyl-5-nitropyrrole-2-carboxylic acid was chromatographed with petroleum ether:ether (95.5) and N-methyl-4-mitropyrrole-2-carboxylic acid was eluted with petroleum ether:ether (25:75). N-methyl-4-nitropyrrole-2-carboxyl chloride was prepared by refluxing one equivalent of N-methyl-4-nitropyrrole-2-carboxylic acid with four equivalents of thionyl chloride for 4h, followed by removal of excess thionyl chloride under vacuum. The nitro acid 5 was obtained in 30% overall yield: IR (KBr) 1690, 1650, 1600, 1565, 1530, 1500, 1310, 1215, 1110 cm$^{-1}$; NMR (DMSO—d$_6$) δ3.84 (s,3), 3.87 (s,3), 3.97 (s,3), 6.85 (s 1), 7.1 (s,1), 7.25 (s,1), 7.26 (s,1), 7.45 (s,1), 7.65 (s.1), 8.2 (s,1), 9.95 (s,1), 10.35 (s,1); UV (H$_2$O) 291 nm (35,600), 236.

EDTA-triethyl ester 9

To a solution of 10 g (0.034 mol) EDTA in 250 mL dry ethanol was added with stirring 1.5 mL of H$_2$SO$_4$. The reaction was refluxed for 24 hours and the solvent was removed. Saturated aqueous sodium bicarbonate (50 ml) was added followed by 250 mL dichloromethane. The layers were separated and the organic layer was washed three times with saturated aqueous sodium bicarbonate, two times with water, dried (Na$_2$SO$_4$), and concentrated to afford 11 g (80%) of the crude tetraethylester. The triethyl ester 9 was prepared according to the procedure of Hay and Nolan, R. W. Hay, K. B. Nolan, *J. Chem. Soc Dalton*, 1348 (1975). To a solution of the unpurified tetraester and 4.6 g (0.027 mol) of cupric chloride dihydrate in 500 mL water was added with stirring 1.3 g (0.032 mol) f sodium hydroxide in 7 mL water at such a rate as to maintain the pH at ca. 5. The solution was then treated with H$_2$S and filtered. The filtrate was concentrated and purified by flash chromatography on silica gel with 10% methanol in dichloromethane to yield 9 g (90%) of the triethylester 9: IR(CH$_2$Cl$_2$) 3000, 1745, 1380, 1210 cm$^{-1}$; NMR (CHCl$_3$)δ1.3 (t,9), 3.25 (m,4), 3.7 (m,8), 4.2 (m,6) m/e 376 (M$^+$); tlc (silica gel, 10% MeOH in CH$_2$Cl$_2$)R$_f$=0.55.

EDTA-triethylester-linker 10

To a solution of 5 g (0.013 mol) EDTA-triethylester 9 and 1.52 g (0.13 mol) N-hydroxysuccinimide G. W. Anderson, J. E. Zimmerman, F. M. Callahan, *J. Am. Chem. Soc.*, 86, 1839 (1964) in 100 mL dioxane was added with stirring 2.7 g (0.013 mol) of dicyclohexylcarbodiimide in 20 mL dioxane. The solution was stirred for 12 hours, filtered and the filtrate concentrated. This residue was dissolved in 100 mL of dimethoxyethane and added with stirring to a solution of 2 g (0.02 mol) of 4-aminobutyric acid and 1.68 g (0.02 mol) of sodium bicarbonate in 100 mL water. After 12 hours the solvent was removed in vacuo and the residue purified by flash chromatography on silica gel with 10% methanol in dichloromethane to give 4 g (65%) of 10: IR (CH$_2$Cl$_2$) 3000, 1740, 1665, 1210 cm$^{-1}$; NMR (DMSO—d$_6$) 1.10 (t,9), 1.63 (m,2), 2.2 (t,2), 2.2 (t,2), 2.7 (t.2), 3.1 (m,2), 3.19 (s,2), 3.45 (s,2), 3.53 (s,4), 4.08 (m,6), 8.0 (t,1); m/e 461 (M+).

Nitro amine 6

To a solution of 2.5 g (6.0 mmol) nitro acid 5, 0.68 g (6.6 mmol) 3-dimethylaminopropylamine, and 0.89 g (6.6 mmol) N-hydroxybenzotriazole, W. Koenig R. Geiger, *Chem. Ber.*, 103, 788 (1970), in 10 mL dimethylformamide was added with stirring at 0° C. 1.36 g (6.6 mmol) dicyclohexylcarbodiimide. The solution was stirred at 0° C. for 1 hour and 25° C. for 12 hours. The dimethylformamide was removed under high vacuum at 35° C., and the residue purified by flash chromatography on silica gel with 3% concentrated aqueous ammonia in methanol to give 2.1g (70%) of nitro amine 6: IR(KBr) 3130, 2950, 1638, 1580, 1530, 1500, 1308, 1250 cm$^{-1}$; NMR (DMSO—d$_6$) δ1.6 (m,2), 2.15 (s,6), 2.28 (t,2), 3.2 (m,2) 3.8 (s,3), 3.95 (s,3), 6.85 (s,1), 7.05 (s,1), 7.2 (s,1), 7.27 (s,1), 7.6 (s,1) 8.05 (t,1), 8.15(s,1), 9.95 (s,1), 10.35 (s,1); UV (H$_2$O) 286 nm, 238; m/e 499 (M+).

Diamine 7

The nitro amine 6 was reduced to the diamine 7 with hydrogen over palladium catalyst 5% in dimethyl formamide

Distamycin-EDTAOtriethylester 11

A solution of 1 g (2.0 mmol) of nitro amine 6 in 20 mL dimethylformamide was hydrogenated over 200 mg of 5% palladium on charcoal at atmospheric pressure for 12 hours. The mixture was filtered through Celite affording the crude amine 7. To a solution of 0.93 g (2.0 mmol) acid 10 in 25 mL dimethylformamide was added with stirring 0.36 g (2.2 mmol) of N,N'-carbonyldiimidazole in 5 mL dimethylformamide. After 2 hours, amine 7 was added and the resulting solution was stirred for 12 hours. Dimethylformamade was removed under high vacuum at 35° C. and the residue purified by flash chromatography on silica gel with 3% concentrated aqueous ammonia in methanol to yield 0.9 g (48%) 11: IR(KBr) 2940, 1730, 1650, 1570, 1530, 1460, 1430, 1400, 1250, 1200 cm$^{-1}$; NMR (DMSO—d$_6$) δ1.19 (t,9), 1.6 (m,2), 1.75 (m,2), 2.13 (s,6), 2.2 (t,2), 2.26 (t,2), 2.7 (m,4), 3.1 (m,2), 3.2 (m,2), 3.2 (s,2), 3.45 (s,2), 3.55 (s,4), 3.84 (s,3), 3.88 (s,3), 3.90 (s,3), 4.08 (m,6), 6.8 (s,1), 6.86 (s,1), 7.0 (s,1), 7.16 (s,1), 7.18 (s,1 ), 7.22 (s,1), 8.0 (t,1), 8.05 (t,1), 9.8 (t,1), 9.88 (t,1), 10.37 (s,1); UV (H$_2$O) 298 nm, 234; m/e 912 (M+).

Distamycin-EDTA 3

To a solution of 0.25 g (0.37 mmol) 11 in 5 mL ethanol was added with stirring 5 mL of 0.5M aqueous lithium hydroxide. The resulting solution was stirred for 12 hours and acidified to pH 4 with 10% aqueous hydrochloric acid. The solvent was removed under vacuum at 35° C. and the residue purified by flash chromatography on silica gel with 20% concentrated aqueous ammonia in ethanol. Final purification was carried out by loading the product dissolved in water. on to an Amberlite XAD-2 column and washing with 2L of water. Elution with 0.1% HCl in methanol afforded 0.15 g (66%) 3: IR(KBr): 2960, 1730, 1640, 1565, 1550, 1465, 1435, 1260, 1210, 1105 cm$^{-1}$; NMR (DMSO—d$_6$): δ1.73 (m,2), 1.85 (m,2), 2.3 (t,2), 2.72 (s,6) 3.05 (t,2), 3.13 (m,2), 3.22 (m.2), 3.4 (t,2), 3.45 (t,2), 3.8 (s,3), 3.82 (s,3), 3.83 (s,3), 3.93 (s.4), 4.04 (s,2), 4.17 (s,2), 6.91 (s.1), 6.93 (s,1), 7.05 (s,1), 7.18 (s,1), 7.22 (s,1), 7.26 (s,1), 8.25 (t,1), 8.86 (t,1), 9.95 (s,1), 9.97 (s,1), 10.15 (s,1), UV (H$_2$O: 297 nm (35,600), 236 (29,400; m/e 866 (C$_{37}$H$_{53}$N$_{11}$O$_{11}$K+).

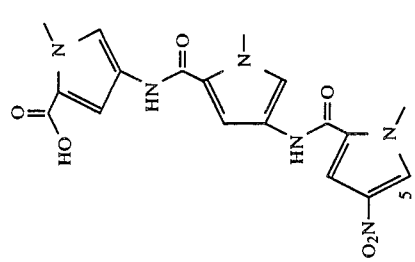 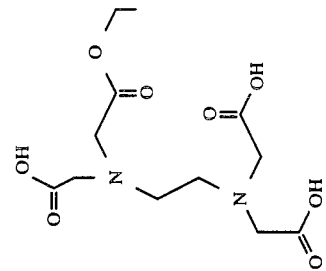
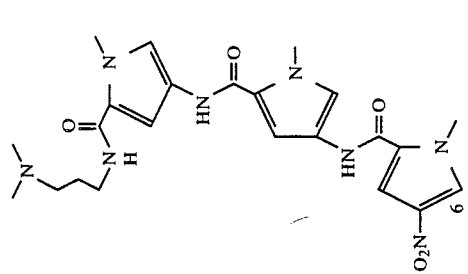 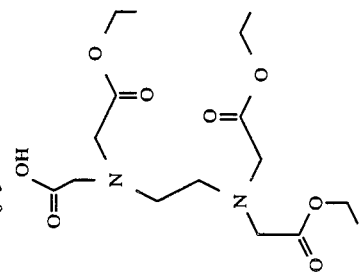
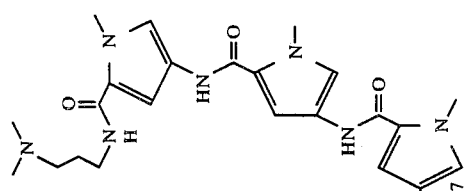
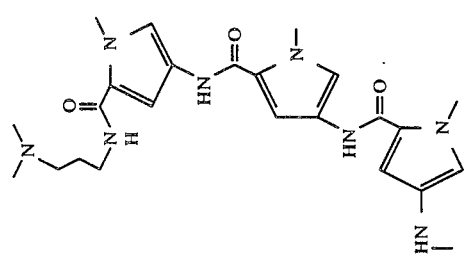 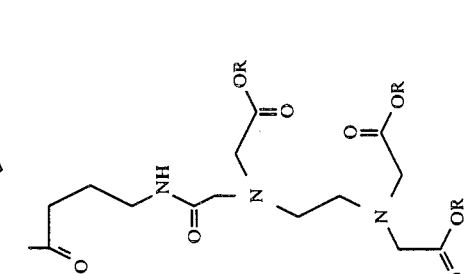

EXAMPLE IV

Synthesis of EDTA-Distamycin

Nitro amine 12

To a solution of 2.5 g (6.0 mmol) nitro acid 5 in 50 ml dimethylformamide was added with stirring 1.07 g (6.6 mmol) of N,N'-carbonyldiimidazole, R. Paul, G. W. Anebrison, *J. Org. Chem.*, 27, 2094 (1962), in 10 mL dimethylformamide. After 2 hours, 9.6 g (66 mmol) of 3,3'-diamino-N-methyl-dipropylamine was quickly added and the resulting solution was stirred for 12 hours. The dimethylformamide was removed under high vacuum at 35° D. and the residue was triturated three times with ether. The crude product was purified by flash chromatography on silica gel with 12% concentrated aqueous ammonia in methanol to yield 2.3 g (68%) of the nitro amine 12: IR(KBr) 2960, 1640, 1580, 1530, 1311, 1210 cm$^{-1}$; NMR (DMSO—d$_6$) $\delta$1.46 (m,2), 1.6 (m,2), 2,12 (s,3), 2.33 (t,4), 2.55 (s,2), 3.2 (m,4), 3.80 (s,3), 3.86 (s,3), 3.96 (s,3), 6.8 (s,1), 7.04 (s,1), 7.2 (s,1) 7.27 (s,1), 7.6 (s,1), 8.05 (t,1), 8.2 (s,1), 0.94 (s,1), 10.3 (s,1); UV (H$_2$O) 294 nm, 239, m/e 542 (M+).

Nitro EDTA-triethylester 13

To a solution of 1.39 g (3.7 mmol) acid 9 in 25 mL dimethylformamide was added with stirring 0.66 g (4.07 mmol) of N,N'-carbonyldiimidazole in 5 mL dimethylformamide. After 2 hours, 2 g (3.7 mmol) of nitro-amine 12 was added and the resulting solution was stirred for 12 hours. Dimethylformamide was removed under high vacuum at 35° C. and purified by flash chromatography on silica gel with 3% concentrated aqueous ammonia in ethanol to yield 2.5 g (75%) of 13: IR(KBr) 2950, 1735, 1640, 1590, 1525, 1500, 1438, 1400, 1310, 1255, 1210; NMR (DMSO—d$_6$) $\delta$1.15 (t,9), 1.55 (m,2), 1.6 (m,2), 2.12 (s,3), 2.7 (m,4), 3.12 (m,2), 3.18 (s.2), 3.20 (m,2), 3.44 (s,2) 3.5 (s,4), 3.8 (s,3), 3.86 (s,3), 3.97 (s,3), 4.05 (m,6), 6.82 (s,1), 7.05 (s,1), 7.27 (s,1), 7.59 (s,1), 7.96 (t,1), 8.03 (t,1), 8.03 (t,1), 8.18 (s,1) 8.56 (s,1), 8.9 (s,1); UV (H$_2$O) 288 nm, 240; m/e 900 (M+).

EDTA-DistamycinOtriethylester 14

A solution of 1 g (1.11 mmol) 13 in 10 mL dimethylformamide was hydrogenated over 200 mg of 5% palladium on charcoal at atmospheric pressure for 12 hours. The mixture was filtered through Celite affording the crude amine 15. To a solution of 0.08 g (1.33 mmol) acetic acid in 3 mL dimethylformamide was added with stirring 0.22 g (1.33 mmol) of N,N'-carbonyldiimidazole in 3 mL dimethylformamide. After 2 hours, amine 15 was added and the resulting solution was stirred to 12 hours. Dimethylformamide was removed under high vacuum at 35° C. and the residue purified by flash chromatography on silica gel with 2% concentrated aqueous ammonia in methanol to yield 0.55 g (54%) of 14: IR(KBr) 2950, 1730, 1650, 1580, 1550, 1535, 1460, 1440, 1400, 1260, 1210 cm$^{-1}$; NMR (DMSO—d$_6$) $\delta$1.17 (t,9), 1.55 (m,2), 1.6 (m,2), 1.97 (s,3), 2.12 (s,3), 2.12 (s,3), 2.28 (m,4), 2.65 (m,2), 2.70 (m,2), 3.12 (m.2), 3.17 (s,2), 3.17 (s,2), 3.44 (s,2), 3.5 (s,4), 3.85 (s,3), 3.88(s,3), 3.9(s,3), 6.8(s,1), 6.84 (s,1), 6.98 (s,1) 7.02 (s,1), 7.14 (s,1), 7.17 (s,1), 7.17 (s,1), 7.22 (s,1), 7.62 (s,1), 7.97 (t,1), 8.02 (t,1), 9.83 (s.1), 9.9 (s,1); UV (H$_2$O) 304 nm, 235; m/e 912 (M+).

EDTA-Distamycin 4

To a solution of 0.25 g (0.27 mmol) 14 in 5 mL ethanol was added with stirring 5 mL of 0.5 M aqueous lithium hydroxide. The resulting solution was stirred for 12 hours and acidified to pH 4 with 10% aqueous hydrochloric acid. The solvent was removed under high vacuum at 35° C. and the residue purified by flash chromatography on silica gel with 3% concentrated ammonia in methanol to yield 0.17 g (75%) of the ammonium salt of ED 4: IR (KBr) 2950, 1635, 1580, 1460, 1430, 1400, 1255, 1205, 1105 cm$^{-1}$; NMR (D$_2$O) $\delta$1.87 *s,3), 1.9 (m,4), 2.8 (s,3), 2.9–3.13 (m,12), 3.17–3.3 (m,6), 3.53 (s,3), 3.57 (s,3), 3.6 (s,3), 3.67 (s,2), 6.42 (s,1), 6.48 (s,1), 6.56 (s,1), 6.8 (s,1), 6.83 (s,1), 6.87 (s,1), UV (H$_2$O)303 nm (35,000 est.) 235 (29,500 est.); m/e 828 (M+).

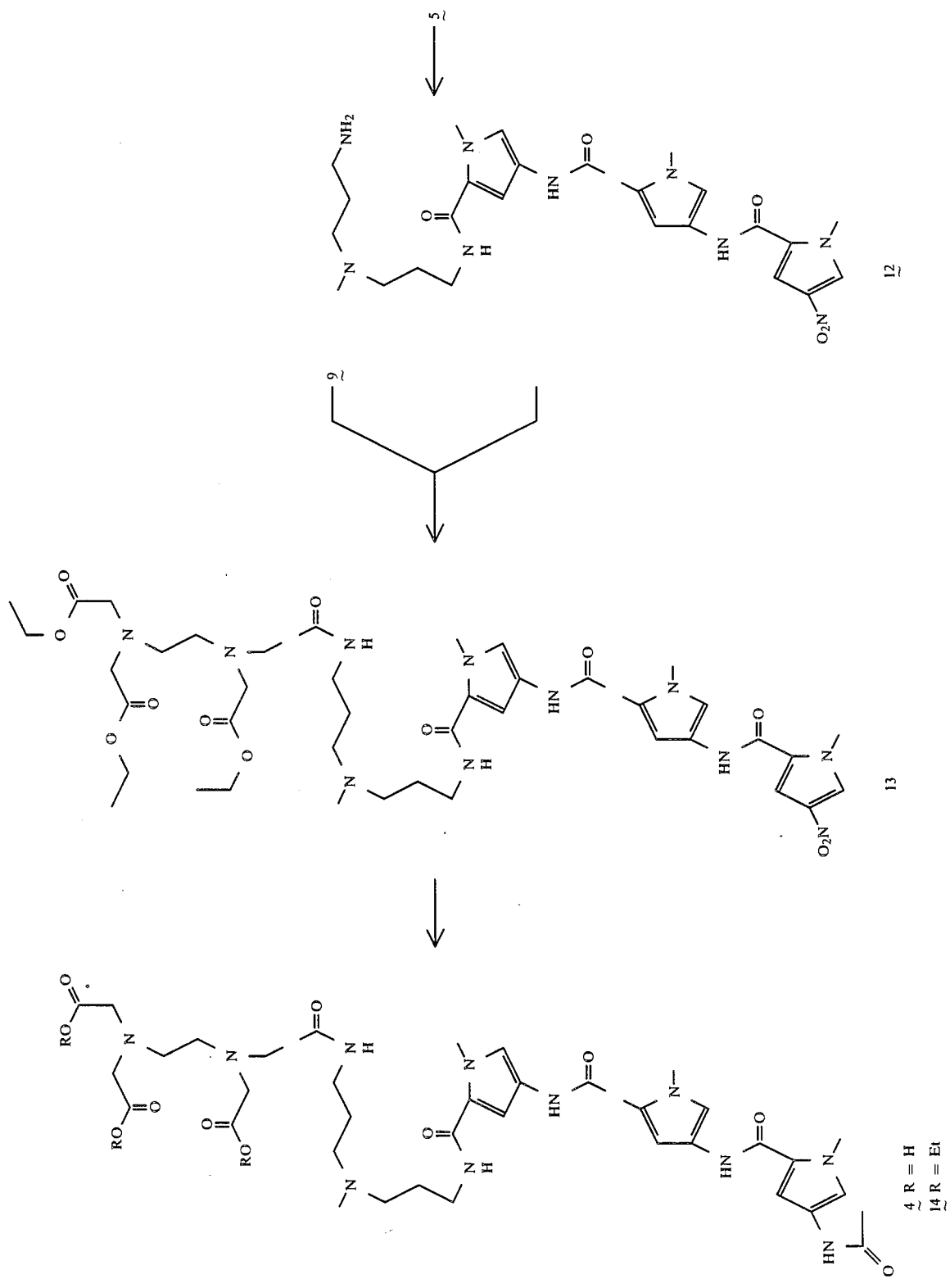

DNA Cleavage Efficiency: DNA cleavage by DE.-Fe(II) and ED.Fe(II) was followed by monitoring the conversion of supercoiled (form I) pBR322 plasmid DNA ($10^{-5}$ M in base pairs) to open circular and linear forms (forms II and III, respectively). (a) J. E. Strong, S. T. Crooke, in "Bleomycin: Chemical, Biochemical, and Biological Aspects", Hecht, S. M., Ed. Springer-Verlag, New York, 1979, p. 244. (b) P. H. Johnson, L. I. Grossman, *Biochemistry*, 16, 4217 (1977). The introduction of one single strand break converts form I to form II. We find that at $10^{-6}$ M concentrations DE.-Fe(II) and ED.Fe(II) in the presence of $O_2$ and DTT cleave DNA, although the cleavage is less efficient than with MPE.Fe(II) or bleomycin.Fe(II) (Table IV).

TABLE IV

Cleavage of pBR322-Plasmid in the Presence of DTT

| Reagent | conc, M | % Form I | II | III |
|---|---|---|---|---|
| EDTA.Fe(II) | $10^{-6}$ | 93 | 7 | 0 |
| DE.Fe(II) | $10^{-6}$ | 30 | 70 | 0 |
| ED.Fe(II) | $10^{-6}$ | 4 | 92 | 4 |
| MPE.Fe(II) | $10^{-7}$ | 0 | 91 | 9 |
| Bleomycin.Fe(II) | $10^{-7}$ | 0 | 48 | 52 |

Form I pBR322 ($10^{-5}$ M bp), DNA cleaving reagent, buffer (10 mM Tris HCl, 50 mM NaCl, pH 7.4) and DTT (1 mM) were allowed to react at 25° D. for 30 minutes and quenched. In all cases reactions were carried to completion. Forms I, II and III were analyzed by agarose gel electrophoresis and quantitated by densitometry after ethidium bromide staining.

Sequence Specific Cleavage: The sequence specific cleavage of heterogeneous double helical DNA by DE.Fe(II) and ED.Fe(II) in the presence of DTT and $O_2$ was examined on three DNA restriction fragments. These fragments (167, 279, and 381 base pairs in length) were prepared by the usual methods from bacterial plasmid pBR322 and were 3' end labeled with $^{32}$P, A. M. Maxam, W. Gilbert, *Methods Enzymol.*, 65, 499 (1980), F. Sanger and A. R. Coulson, *J. Mol. Biol.*, 94, 441-448 (1975). Each DNA cleaving reagent was allowed to react at two different concentrations with each DNA restriction fragment for 30 minutes at 25° C. The samples were frozen, lyophilized, suspended in formamide, and electrophoresed on a 0.4 mm, 9% polyacrylamide/50% urea Maxam-Gilbert sequencing gel capable of resolving DNA fragments differing in length by one nucleotide. An autoradiogram of a Maxam-Gilbert gel was prepared. The MPE.Fe(II) lanes show a uniform DNA cleavage pattern indicative of relatively non-sequence specific cleavage. In contrast, DE.Fe(II) and ED.Fe(II) both show a nonrandom pattern with DNA cleavage confined to highly localized sites. A comparison with the Maxam-Gilbert G-lane reveals the A+T rich sites cleaved by DE.Fe(II) and ED.Fe(II). Importantly, the cleavage patterns of DE.Fe(II) and ED.Fe(II) occur in similar locations but opposite intensity.

167 Restriction Fragment: The 70 bases analyzed from the autoradiogram of the Maxam-Gilbert gel for the 167 base pair restriction fragment show two cleavage sites by DE.Fe(II) and three by ED.Fe(II) (12.5 M concentration formal binding density of 0.125 DE or ED/base pairs). These cleavage sites cover 2–5 contiguous base pairs separated by the sequence 3'-TTT-5' (base pairs 91–93). The cleavage sites flanking this sequence are of unequal intensity. The major cleavage site for DE.Fe(II) is on the 3' end of the 3'-TTT-5 sequence. The major cleavage site for ED.Fe(II) is on the 5 end.

279 Restriction Fragment: The 70 base pairs analyzed from the autoradiogram of the Maxam-Gilbert gel for the 279 base pair restriction fragment shows two cleavage sites by DE.Fe(II) and ED.Fe(II). The cleavage sites covering 3–5 base pairs are of unequal intensity and flank the sequence 3'-ACA-5' (base pairs 125-127). For DE.Fe(II) the major cleavage is on the 5 end of the 3'-ACA-5' sequence and for ED.Fe(II) it is on the 3' end.

381 Restriction Fragment: The 100 bases analyzed from the autoradiogram of the Maxam-Gilbert gel for the 381 base pair restriction fragment show two cleavage sites by both DE.Fe(II) and ED.Fe(II). The cleavage sites covering 3–5 base pairs are of unequal intensity and flank the sequence 3'-TTT-5' (base pairs 124–126). For DE.Fe(II), the major cleavage site is on the 3' end of the 3'-TTT-5' sequence and for ED.Fe(II) it is on the 5' end.

Opposite Strand Analysis: The 381 base pair fragment was labeled at the 5' end of the Bam HI restriction site. The cleavage patterns for DE.Fe(II) and ED.Fe(II) on this 5' end labeled 381 fragment were directly compared to the cleavage patterns labeled on the 3' end of the Bam HI site. The 70 bases analyzed from the autoradiogram of the Maxam-Gilbert gel for the 5' end labeled restriction fragment show a DNA cleavage pattern that is asymmetric, shifted to the 3' end for both DE.Fe(II) and ED.Fe(II)

Preparation of Supercoiled pBR322 and End-Labeled Restriction Fragments

DNA for this investigation was bacterial plasmid pBR322 whose entire sequence is known. J. G. Suttcliffe, *Cold Spring Harbor Symp. Quant. Biol.* 43, 77–90 (1979). The plasmid was grown in *E.coli* strain HB101 and isolated by the methods of Tanaka and Weissblum. T. Tanaka, B. Weisblum, *J. Bacteriol.* 121, 354–362 (1974). Superhelical pBR322 plasmids, containing 98.5% form I DNA, were first digested with the restriction endonuclease Eco RI and then labeled at the 3' end with [$\alpha-^{32}$P]dATP and the Klenow fragment of DNA polymerase I. F. Sanger and A. R. Coulson, *J. Mol. Biol.*, 94, 441–448 (1975). A second enzymatic digest with the restriction endonuclease Rsa I yielded two end labeled fragments, 167 and 516 nucleotides in lengths. These were isolated by gel electrophoresis on a 5% polyacrylamide, 1:30 crosslinked, 2 mm thick gel. Isolation of the two fragments from the gel and subsequent procedures were similar to those of Maxam-Gilbert. A. M. Maxam, W. Gilbert, *Methods Enzymol.*, 65, 499 (1980). In a similar fashion, pBR322 was restricted with Bam HI and labeled at the 3' end. Further restriction with Eco RI and Sal I yielded a 381 and a 279 base pair fragment, respectively. The 381 base pair was 5'labeled at the Bam HI site by cleavage of pBR322 with Bam HI, treatment with bacterial alkaline phosphatase, followed by treatment with 5'($\alpha^{32}$P)-ATP and polynucleotide kinase. Further restriction with Eco RI yielded the desired fragment.

Cleavage Reactions

All reactions were run with freshly prepared drug-iron complexes. Equimolar drug-iron(II) complexes were made by combining aqueous drug stock solutions (~10 mM, checked spectrophotometrically before use) with a 10 mM aqueous ferrous ammonium sulfate solution and then diluting with water to the appropriate drug-iron concentration. The cleavage reactions were initiated by adding 2 μl of a buffered DNA solution (final concentrations and buffers are in figure legends) followed by 2 μl of an aqueous 10 mM DTT solution. The reactions were thoroughly mixed by vortexing, spun down and incubated at 25° C. for 30 minutes.

Analysis of the Cleavage Efficiency

The cleavage reactions were conducted with 10 μM pBR322 superhelical DNA containing >98% form I DNA. After ½ hour at 25° C. the reactions were quenched with 4 μl of a 50 mM disodium EDTA, 10% ficol solution and electrophoresed on a 1% agarose gel at 120 V for 4 hours. The gel was then stained with ethidium bromide, destained and photographed with polaroid type 55 positive-negative land film under long wavelength UV irradiation. The negative film was then scanned at 485 nm on a Cary 219 spectrophotometer and the peak areas of the form I, II and III bands were determined by a gel scanning program. The data was then corrected for the decreased stainability of form I DNA and for the presence of 1.5% form II in the original sample.

Analysis of the Sequence Specificity of the Cleavage Reactions

The cleavage reactions were run with >600 cpm of $^{32}P$ 3' end labeled restriction fragments made up to a total DNA concentration of 100 μM (bp) with sonicated calf thymus DNA. The reactions were run at 25° C. for ½ hour and terminated by lyophilization and suspension in 4 l of a pH 8.3 100 mM Tris-Borate, 50% formamide solution. These were then loaded on a 0.4 mm thick, 40 cm long, 8% polyacrylamide, 1:20 crosslinked, 50% urea gel and electrophoresed at 1500 V until xylene cylanol tracking dye was at the bottom of the gel. Autoradiography of the gels was carried out at −50° C. on Kodak, X-Omat AR film and the autoradiograms were then scanned at 485 nm. The relative peak area for a particular site was equated to the relative cleavage efficiency.

EXAMPLE V

Penta-N-methylpyrrolecarboxamide-EDTA (P5E) was synthesized and purified by procedures analogous to those described for distamycin-EDTA (DE) and EDTA-distamycin (ED) above. The NMR, IR, UV, and mass spectral data are consistent with the assigned structure which is as follows:

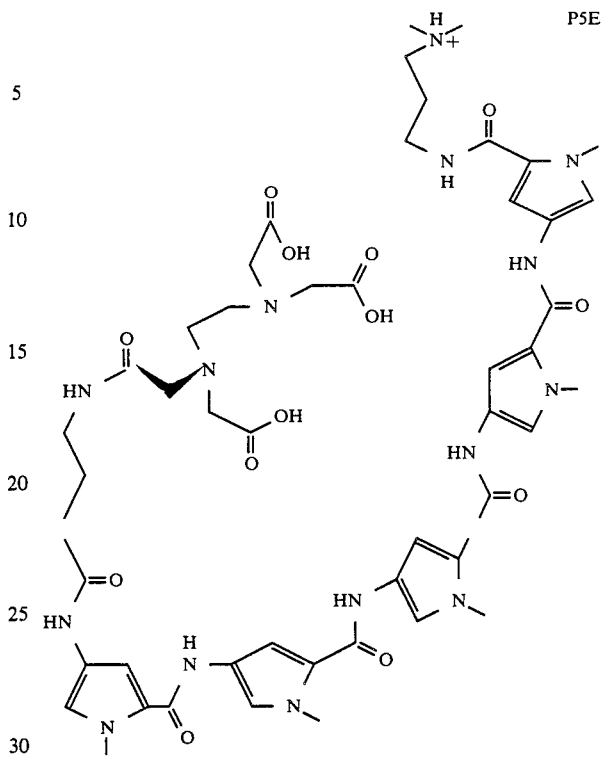

N-Methyl-4-[N-methyl-4(N-methyl4-nitropyrrole-2-carboxamide)-pyrrole-2-carboxamide]-pyrrole-2-carboxylic acid and N-Methyl-4-[N-methyl-4-(N-methyl-4-nitropyrrole-2-carboxamide)-pyrrole-2-carboxyamide]-pyrrole-2-carboxamide-dimethylpropylamine, compounds 2 and 11, respectively, in the following reaction schemes were prepared as disclosed by Bailer M. et al, J. Tetrahydron (1978) Vol. 34, p. 2389 et seq.

EDTA-triethyl ester 9—To a solution of 10 g (0.034 mol) EDTA in 250 mL dry ethanol was added with stirring 1.5 mL of $H_2SO_4$. The reaction was refluxed for 24 hours and the solvent was removed. Saturated aqueous sodium bicarbonate (50 ml) was added followed by 250 mL dichloromethane. The layers were separated and the organic layer was washed three times with saturated aqueous sodium bicarbonate, two times with water, dried ($Na_2SO_4$), and concentrated to afford 11 g (80%) of the crude tetraethylester. The triethyl ester 9 was prepared as follows. To a solution of the unpurified tetraester and 4.6 g (0.027 mol) of cupric chloride dihydrate in 500 mL water was added with stirring 1.3 g (0.032 mol) of sodium hydroxide in 7 mL water at such a rate as to maintain the pH at ca. 5. The solution was then treated with $H_2S$ and filtered. The filtrate was concentrated and purified by flash chromatography on silica gel with 10% methanol in dichloromethane to yield 9 g (90%) of the triethylester 9: IR($CH_2Cl_2$) 3000, 1745, 1380, 1210 cm$^{-1}$; NMR (CHCl$_3$) δ1.3 (t,9H,J=7 Hz)), 2.75 (s.4H), 3.3 (s,2H), 3.4 (s,4H), 3.5 (s,4H), 4.1 (q,4H,J=7 Hz); m/e 376 (M+); tlc (silica gel, 10% MeOH in $CH_2Cl_2$) $R_f$=0.55.

EDTA-triethylester-linker 5—To a solution of 5 g (0.013 mol) EDTA-triethylester 9 and 1.52 g (0.13 mol) N-hydroxysuccinimide in 100 mL dioxane was added with stirring 2.7 g (0.013 mol) of dicyclohexylcarbodiimide in 20 ml dioxane. The solution was stirred for 12 hours, filtered, and the filtrate concentrated. This residue was dissolved in 100 mL of dimethoxyethane and added with stirring to a solution of 2 g (0.02 mol) of 4-aminobutyric acid and 1.68 g (0.02 mol) of sodium bicarbonate in 100 mL water. After 12 hours the solvent was removed in vacuo and the residue purified by flash chromatography on silica gel with 10% methanol in dichloromethane to give 4 g (65%) of 5: IR (CH$_2$Cl$_2$) 3000, 1740, 1665, 1210 cm$^{-1}$; NMR (DMSO—d$_6$) $\delta$1.19 (t,9H,J=Hz) 1.63 (m,2), 2.2 (t,2H,J=6 Hz), 2.7 h(t,2H,J=6 Hz), 3.1 (m,2H), 3.19 (s,2H), 3.45 (s,2H), 3.53 (s,4H), 4.08 (m,6H) 8.0 (t,1H); m/e 461 (M+).

Distamycin-EDTA-triethylester—A solution of 1 g (2.0 mmol) of nitro amine 11 in 20 mL dimethylformamide was hydrogenated over 200 mg of 5% palladium on charcoal at 52 psi hydrogen on a Parr rocker for 12 hours. The mixture was filtered through Celite and the celite was washed with 25 ml DMF affording a solution of the crude amine 3. To a solution of 0.93 g (2.0 mmol) acid 10 g in 25 mL dimethylformamide was added with stirring 0.36 g (2.2 mmol) of N,N'-carbonyldiimidazole in 5 mL dimethylformamide. After 2 hours, amine 3 was added and the resulting solution was stirred for 12 hours. Dimethylformamide was removed under high vacuum at 35° C. the residue triturated three times with ether and purified by flash chromatography on silica gel with 3% concentrated aqueous ammonia in methanol to yield 0.9 g (48%) distamycin-EDTA-triethylester: IR(KBr) 2940, 1730, 1650, 1570, 1530, 1460, 1430, 1400, 1250, 1200 cm$^{-1}$; NMR (DMSO—d$_6$) $\delta$1.19 (t,9H,J=7 Hz), 1.6 (m,2H), 1.75 (m,2H), 2.13 (s,6H), 2.2 (t,2H,J=7 Hz), 2.26 (t,2H,J=7 Hz), 2.7 (m, 4H), 3.1 (m,2H), 3.2 (m,2H),3.2 (s,2H), 3.45 (s,2H),3.55 (s,4H),3.84 (s,3H) 3.88 (s,3H), 3.90 (s,3H), 4.08 (q,6H,J=Hz), 6.8 (d,1H), 6.86(d,1H), 7.0 (d,1H), 7.16 (d,1H), 7.18 (d,1H), 7.22 (d,1H), 8.0 (t,1H), 9.8 (t,1H), 9.88 (t,1H), 10.37 (d,1H); UV (H$_2$O) 298 nm, 234; m/e 912 (M+).

Distamycin-EDTA 1—To a solution of 0.25 g (0.37 mmol) distamycin-EDTA-triethylester: in 5mL ethanol was added with stirring 5mL of 0.25M aqueous lithium hydroxide. The resulting solution was stirred to 12 hours and acidified to pH 4 with 10% aqueous hydrochloric acid. The solvent was removed under vacuum at 35° C., the residue triturated three times with ether and purified by flash chromatography on silica gel with 20% concentrated aqueous ammonia in ethanol. Final purification was carried out by loading the product dissolved in water on to an Amberlite XAD-2 column and washing with 13% aqueous Na$_2$EDTA and 2 l doublly distilled water. Elution with methanol afforded 0.15 g (66%) 1: IR(KBr): 2960, 1730, 1640, 1565, 1550, 1465, 1435, 1260, 1210, 1105 cm$^{-1}$: NMR (DMSO—d$_6$): $\delta$1.73 (m,2H), 1.85 (m,2H), 2.3 (t,2H,J=Hz), 2.72 (s,6H), 3.05 (t,2H,J=Hz), 3.13 (m,2H), 3.22 (m,2H), 3.4 (d,2H,J=6 Hz), 3.45 (d,2H,J=6 Hz), 3.8 (s,3H), 3.82 h(s,3H), 3.83 (s,3H), 3.93 (s,4H), 4.04 (s,2H), 4.17 (s,2H), 6.91 (s,1H), 6.93 (s,1H), 7.05 (s,1H), 7.18 (s,1H), 7.22 (s,1H), 7.26 (s,1H), 8.25 (t,1H), 8.86 (t,1H), 9.95 (s,1H), 9.97 (s,1H), 10.15 (s,1H); UV (H$_2$O): 297 nm (35,600), 236 (29,400); m/e 866 (C$_{37}$H$_{53}$N$_{11}$O$_{11}$K$^+$).

Nitro amine 8—To a solution of 2.5 g (6.0 mmol) nitro acid 2 in 50 mL dimethylformaide was added with stirring 1.07 g (6.6 mmol) of N,N -carbonyldiimidazole in 10 mL dimethylformamide. After 2 hours, 9.6 g (66 mmol) of 3,3'-diamino-N-methyl-dipropylamine was quickly added and the resulting solution was stirred for 12 hours. The dimethylformamide was removed under high vacuum at 35° C. and the residue was triturated three times with ether. The crude product was purified by flash chromatography on silica gel with 12% concentrated aqueous ammonia in methanol to yield 2.3 g (68%) of the nitro amine 8: IR(KBr) 2960, 1640, 1580, 1530, 1311, 1210 cm$^{-1}$; NMR (DMSO—d$_6$) $\delta$1.46 (m,2H), 1.6 (m,2H), 2.12 (s,3H), 2.33 (t,4H,J=7 Hz), 2.55 (s,2H), 3.2 (m,4H), 3.80 (s,3H), 3.86 (s,3H), 3.96 (s,3H), 6.8 (d,1H,J=1.5 Hz), 7.04 (d,1H,J=1.5 Hz), 7.2 (d,1H,J=1.5 Hz), 7.27 (d,1H,J=1.5 Hz), 7.6 (d,1H,H=1.5 Hz), 8.05 (t,1H,J=6 Hz), 8.2 (d,1H,J=1.5 Hz), 9.94 (d,1h), 10.3 (d,1h); UV (H$_2$O) 294 nm, 239; m/e 542 (M+).

Nitro EDTA-triethylester 10—To a solution of 1.39 g (3.7 mmol) acid 9 in 25 mL dimethylformamide was added with stirring 0.66 g (4.07 mmol) of N,N'-carbonyldiimidazole in 5 mL dimethylformamide. After 2 hours, 2 g (3.7 mmol) of nitroamine 8 was added and the resulting solution was stirred for 12 hours. Dimethylformamide was removed under high vacuum at 35° C. the residue triturated three times with ether and purified by flash chromatography on silica gel with 3% concentrated aqueous ammonia in ethanol to yield 2.5 g (75%) of 10: IR(KBr) 2950. 1735, 1640, 1590, 1525, 1500, 1438, 1400, 1310, 1255, 1210; NMR (DMSO—d$_6$) $\delta$1.15 (t,9H,J=7 Hz), 1.55 (m,2H), 1.6 (m,2H), 2.12 (s,3H), 2.7 (m,4H), 3.12 (m,2H), 3.18 (s,2H), 3.20 (m,2H), 3.44 (s,2H), 3.5 (s,4H), 3.8 (s,3H), 3.86 (s,3H), 4.05 (q,6H,J=7 Hz), 6.82 (d,1H,J=1.5 Hz), 7.05 (d,1H,J=1.5 Hz), 7.19 (d,1H,J=1.5 Hz), 7.27 (d,1H,J-1.5 Hz), 7.59 (d,1H,J=1.5 Hz), 7.96 (t,1H,J-7 Hz), 8.03 (t,1H,J=7 Hz), 8.18 (d,1H,J=1.5 Hz), 8.56 (d,1), 8.9 (d,1); UV (H$_2$O) 288 nm, 40., m/e 900 (M+).

EDTA-Eistamycin-triethylester 7—A solution of 1 g (1.11 mmol) 10 in 10 mL dimethylformamide was hydrogenated over 200 mg of 5% palladium on charcoal at 52 psi hydrogen on a Parr rocker for 12 hours. The mixture was filtered through Celite and the celite was washed with 25 ml DMF to afford the crude amine which is the reduced form of compound 10. To a solution of 0.08 g (1.33 mmol) acetic acid in 3mL dimethylformamide was added with stirring 0.22 g (1.33 mmol) of N,N'-carbonyldiimidazole in 3 mL dimethylformamide. After 2 hours, crude amine which is the reduced form of compound 10 was added and the resulting solution was stirred for 12 hours. Dimethylformamide was removed under high vacuum at 35° C., the residue triturated three times with ether and purified by flash chromatography on silica gel with 2% concentrated aqueous ammonia in methanol to yield 0.55 g (54%) of 7: IR(KBr) 2950, 1730, 1650, 1580, 1550, 1535, 1460, 1440, 1400, 1260, 1210 cm$^{-1}$; NMR (DMSO—d$_6$) $\delta$1.17 (t,9H,J=7 Hz), 1.55 (m,2H), 1.6 (m,2H), 1.97 (s,3H), 2.12 (s,3H), 2.28 (m,4H), 2.65 (m,2H), 2.70 (m,2H), 12 (m,2H), 3.17 (s,2H), 3.17 (m,2H), 3.44 (s,2H), 3.5 (s,4H), 3.85 (s,3H), 3.88 (s,3H), 3.9 (s,3H), 4.08 (q,6H,J=7 Hz), 6.8 (d,1H), 6.84 (d,1H), 6.98 (d,1H), 7.02 (d,1H), 7.14 (d,1H), 7.17 (d,1H), 7.22 (d,1H), 7.62 (d,1H), 7.97 (t,1H,J=7 Hz), 8.02 (t,1H,J=7 Hz), 9.83 (d,1H), 9.9 (d,1H); UV (H$_2$O) 304 nm 235; m/e 912 (M+).

EDTA-Distamycin 6—To a solution of 0.25 g (0.27 mmol) 7 in 5 mL ethanol was added with stirring 5mL of 0.25M aqueous lithium hydroxide. The resulting solution was stirred for 12 hours and acidified to pH a with 10% aqueous hydrochloric acid. The solvent was removed under high vacuum at 35° C. and the residue purified by flash chromatography on silica gel with 3% concentrated ammonia in methanol to yield 0.17 g (75%) of the ammonium salt of ED 6: IR (KBr) 2950, 1635, 1580, 1460, 1430, 1400, 1255, 1205, 1105 cm$^{-1}$; NMR (D$_2$O) δ1.87 (s,3H), 1.9 (m,4H), 2.8 (s,3H), 2.9–3.13 (m,12H), 3.17–3.3 (m,6H), 3.53 (s,3H), 3.57 (s,3H), 3.6 (s,3H), 3.67 (s,2H), 6.42 (d,1H), 6.48 (d,1H), 6.56 (d,1H), 6.8 (d,1H), 6.83 (d,1H), 6.87 (s,1H); UV (H$_2$O) 303 nm (35,000 est.) 235; m/e 828 (M+).

4-Nitro-tetra-N-methylpyrrole-carboxamide propyl-dimethyl amine 12—A solution of 3 g (6.0 mmol) nitro amine 11 in 25 mL dimethylformamide was hydrogenated over 400 mg of 5% palladium on charcoal at 52 psi hydrogen on a Parr rocker for 12 hours. The mixture was filtered through Celite and the celite was washed with 20 ml dimethylformamide to afford the crude amine. 200 mL of water and 0.6 g (7.2 mmol) NaHCO$_3$ were added with stirring to the filtrate, followed by a solution of 1.35 g (7.2 mmol) N-methyl-4-nitropyrrole-2-carbosylic acid chloride in 10 mL dimethylformamide. The mixture was stirred 12 hours, 200 mL water added and filtered. The product was washed with saturated aqueous sodium bicarbonate, water and dried to afford 2.6 g (70%) of the nitro amine 12 : IR (KBr) 2950, 1630, 1580, 1530, 1465, 1430, 1308, 1255 cm$^{-1}$; NMR (DMSO—d$_6$) δ1.6 (m,2H), 2.2 (s,6H), 2.3 (t,2H,J=7 Hz), 3.2 (m,2H), 3.8 (s,3H), 3.85 (s,3H), 3.88 (s,3H), 3.95 (s,3H), 6.85 (s,1H), 7.07 (m,2H), 7.2 (s,1H), 7.27 (s,1H), 7.31 (s,1H), (s,1H), UV (H$_2$O) 305 nm, 236; m/e 621 (M+).

4-Nitro-penta-N-methylpyrrole-carboxamide propyl-dimethyl amine 13—A solution of 2.6 g (4.2 mmol) nitro-tetrapyrrole amine 12 in 40 mL dimethylformamide was hydrogenated over 400 mg of 5% palladium on charcoal at 52 psi hydrogen on a Parr rocker for 12 hours. The mixture was filtered through Celite and the celite was washed with 10 ml DMF to afford the crude amine. 200 mL of water and 0.42 g (5.0 mmol) NaHC0$_3$ were added stirring to the filtrate, followed chloride in 7mL dimethylformamide. The mixture was stirred for 12 hours and the solvent removed under high vacuum at 35° C. The residue was triturated three times with ether and purified by chromatography on silica gel with 2% concentrated aqueous ammonia (33%) in methanol yielding 1.9 g (61%) of nitro aminde 13 : IR (KBr) 3350, 2945, 1627, 1580, 1530, 1465, 1435, 1307, 1260, 1110 cm$^{-1}$; NMR (DMSO—d$_6$) δ1.65 (m,2H), 2.2 (s,6H), 2.3 (t,2H=J=7 Hz), 3.2 (m,2H), 3.83 (s,3H), 3.9 (s,3H), 3.91 (s,3H), 4.0 (s,3H), 6.85 (s,1H), 7.1 (m,3H), 7.2 (m,3H), 7.27 (m,2H), 7.31 (s,1H), 8.1 (t,1H,J=7 Hz), 8.2 (s,1H), 9.92 (s,1H), 9.97 (s,1H), 10.03 (s,1H), 10.35 (s,1H); UV (H$_2$O) 310 nm, 236; m/e 743 (M+).

Penta-N-methylpyrrole-carboxamide-EDTA triethyl ester 16—A solution of 1 g (1.35 mmol) nitro amine 13 in 20 mL dimethylformamide was hydrogenated over 200 mg of 5% palladium on charcoal at atmospheric pressure for 24 hours. The mixture was filtered through Celite and the celite was washed with 25 ml DMF to afford the crude amine.

To a solution of 0.62 g (1.35 mmol) triethylester 5 in 10 ml dimethylformamide was added with stirring 0.24 g (1.5 mmol) of N,N'-carbonyldiimidazole in 5 mL dimethylformamide. After 2 hours, the reduced nitro compound was added and the resulting solution was stirred for 12 hours. Dimethylformamide was removed under high vacuum at 35° C., the residue was triturated three times with ether and purified by flash chromatography on silica gel with 4% concentrated aqueous ammonia (33%) in ethanol to afford 0.6 g (40%) of P5E ethyl ester 16 : IR (KBr) 2960, 1725, 1650, 1585, 1540, 1470, 1440, 1410, 1260, 1210, 1110 cm$^{-1}$; NMR (DMSO—d$_6$) δ1.2 (t,6H,J=7 Hz), 1.65 (m,2H), 1.74 (m,2H), 2.15 (s,6H), 2.2 (m.2H), 2.3 (t,2H,J=7 Hz), 2.7 (m,4H), 3.1 (m,2H), 3.2 (m,2H), 3.22 (s,2H), 3.45 (s,2H), 3.50 (s,4H), 3.8 (s,3H), 3.87 (m,12H), 4.07 (m,6H), 6.8 (s,2H), 7.07 (m,3H), 7.2 (s,2H), 7.25 (s,3H), 8.1 (t,1H,H=7 Hz) 9.9 (s,1H) 9.95 (s,1H) UV (H$_2$O) 306 nm, 236; m/e 1156 (M+).

Penta-N-methylpyrrole carboxamide-EDTA 15—To a solution of 250 mg (0.23 mmol) P5E triethyl ester 16 in 5 mL ethanol was added with stirring 5mL of 0.25M aqueous lithium hydroxide. The resulting solution was stirred for 12 hours and acidified to pH 4 with 10% aqueous hydrochloric acid. The solvent was removed under high vacuum at 35° C. and the residue purified by flash chromatography on silica gel with 4% concentrated aqueous ammonia (33%) in methanol. Final purification was carried out by loading the product dissolved in water, onto an amberlite XAD-2 column and washing with 1 l of 3% aqueous Na$_2$EDTA and 2 L of water. Elution with methanol afforded 0.17 (73%) P5E 15: IR (KBr) 2950, 1730, 1640, 1570, 1460, 1438, 1430, 1400, 1252, 1205 cm$^{-1}$; NMR (DMSO—d$_6$) 1.77 (m,2H), 1.92 (m,2H), 2.33 (t,2H,J=7 Hz), 2.75 (s,6H), 3.08 (m,2H), 3.24 (m,2H), 3.3 (m,2H), 3.35 (m, 2h), 3.8 (s,3H), 3.87 (m,12H), 3.98 (s,2H), 4.1 (s,2H), 6.95 (m,2H), 7.1 (m,3H), 7.2 (s,1H, 7.22 (s,1H), 7.32 (s,3H), 8.2 (s,1H), 8.65 (s,1H), 9.97 (m,4H), 10.05 (s,1H); UV (H$_2$O) 310 nm (45,000)101 238 nm; m/e 1072 (M+).

Penta-N-methylpyrrole-propyldimethyl amine P5 14—A solution of 250 mg (0.35 mmol) nitro-penta-N-methylpyrrolepropyl dimethyl amine 13 in 20 mL dimethylformamide was hydrogenated over 100 mg of 5% palladium on charcoal at 52 psi hydrogen on a Parr rocker for 12 hours. The mixture was filtered through celite yielding the crude amine. The celite was washed with 10 ml DMF.

To a solution of 0.024 g (0.40 mmol) acetic acid in 3 mL dimethylformamide was added with stirring 0.065 g (0.40 mmol) of N,N'-carbonyldiimidazole in 2 mL dimethylformamide. After 2 hours, the crude amine was added and the resulting solution was stirred for 12 hours. Dimethylformamide was removed under high vacuum at 35° C., the residue was triturated three times with ether and purified by flash chromatography on silica gel with 5% concentrated aqueous ammonia (33%) in ethanol to yield 150 mg (60%) of P514 : IR (KBr) 2940, 16aO, 1580, 1530, 1460, 1430, 1400, 1255, 1200, 1100 cm$^{-1}$; NMR (DMSO—d$_6$) δ1.65 (m,2H), 2.0 (s,3H), 2.2 (s,6H), 2.3 (t,2H,J=7 Hz), 3.2 (m,2H),3.83 (s,3H), 3.9 (m,12H), 6.85 (s,1H) 6.0 (s,1H), 7.07 (m,3H), 7.15 (s,1H), 7.18 (s, 1H), 7.25 (s, 3H), 8.10 (t,1H,J=6 Hz), 9.83 (s,1H), 9.91 (m,2H), 9.97 (s,2H); UV (H$_2$O) 312 nm, (45,000)101 236 nm; m/e 755 (M−).

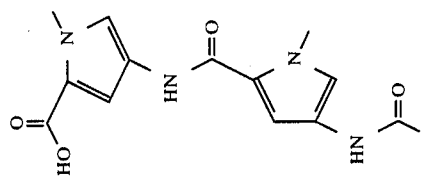
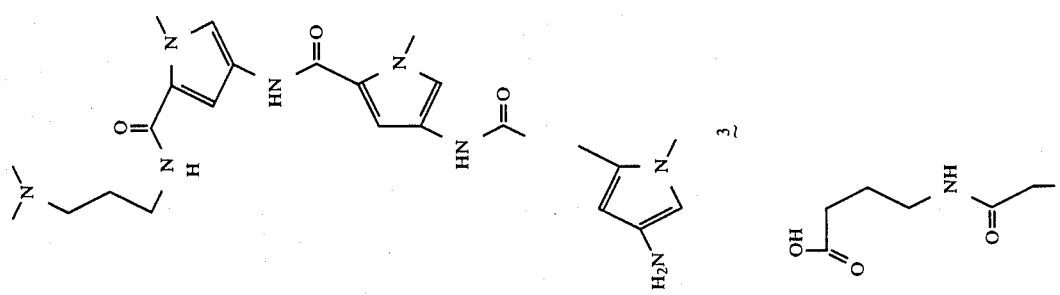
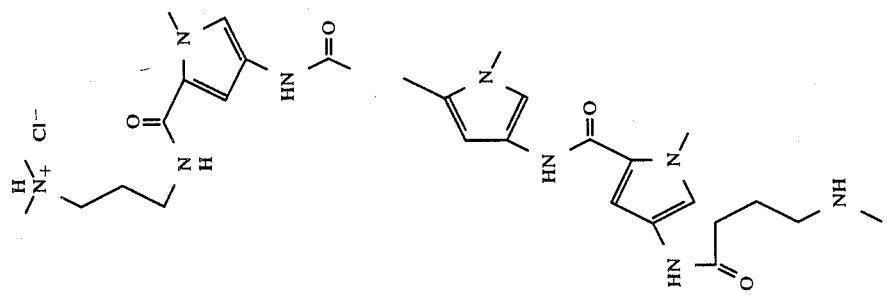

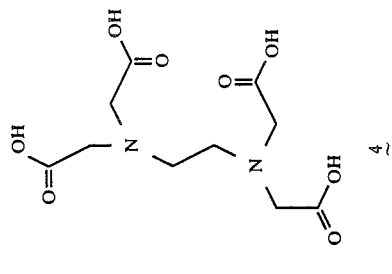
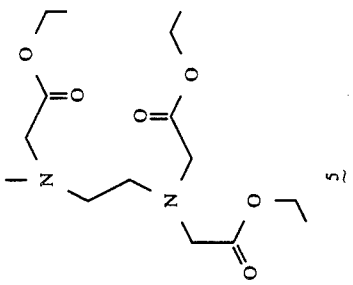
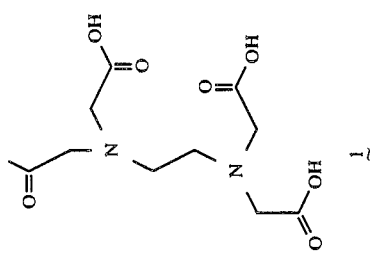
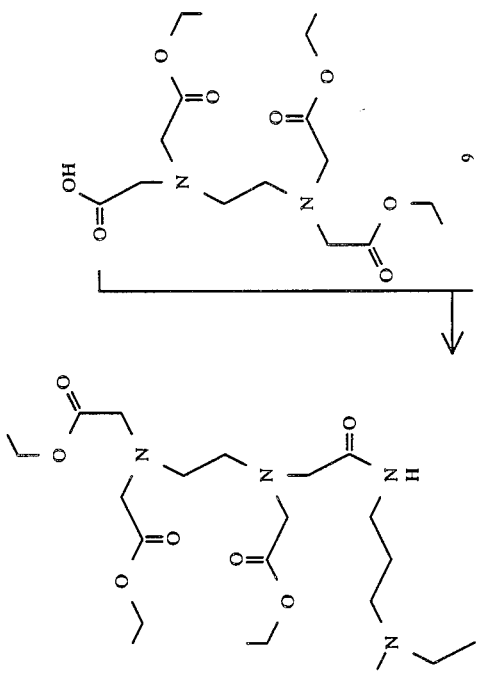
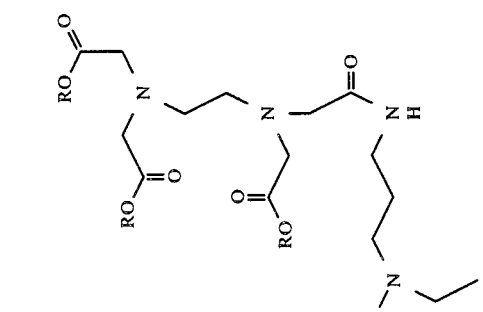
a. $H_2N(CH_2)_3N(CH_3)_2$, HOBt, DCC   b. $H_2$, Pd/C   c. $H_2SO_4$, EtOH   d. $CuCl_2$, NaOH   e. DCC, NHS   f. $H_2N(CH_2)_3CO_2H$, $NaHCO_3$   g. CDI   h. LiOH   i. HCl

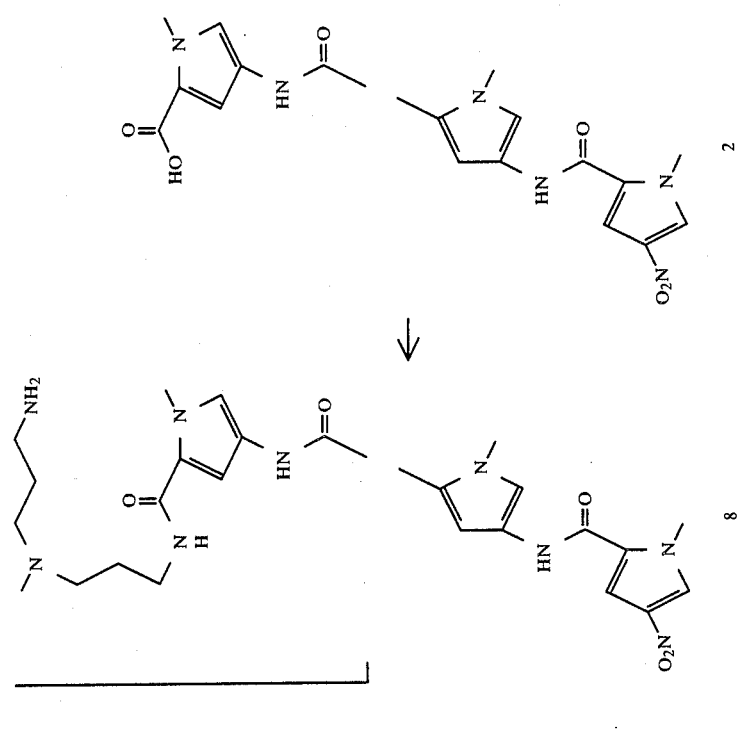
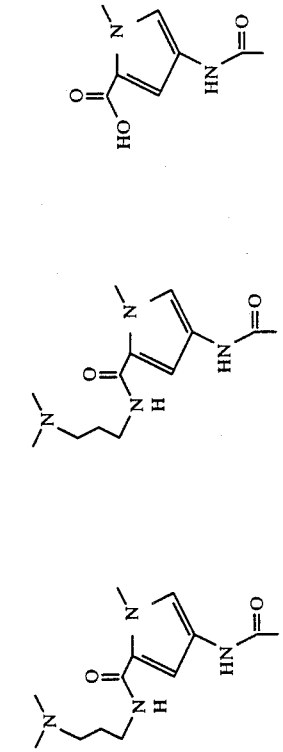
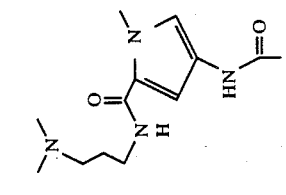
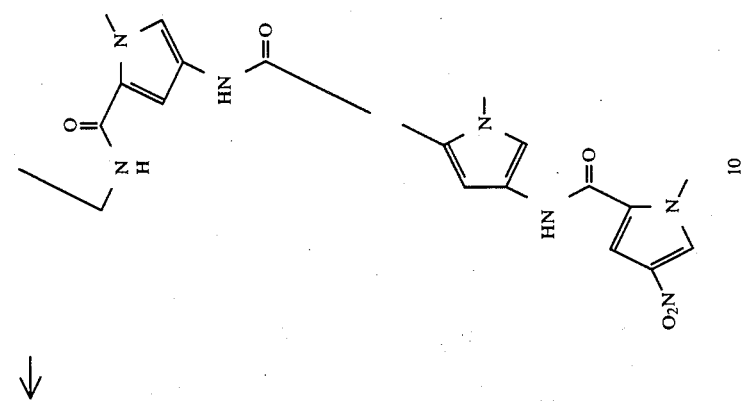
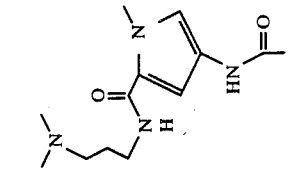
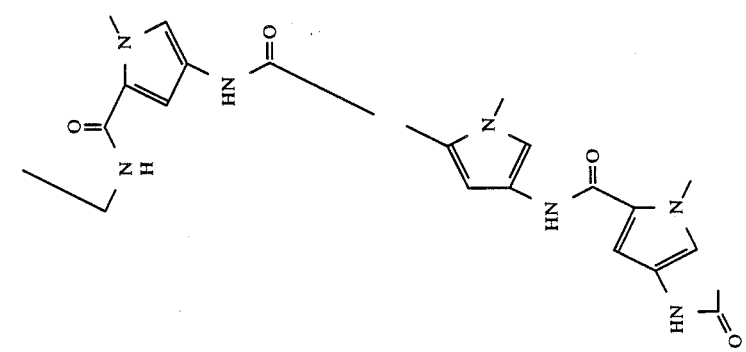

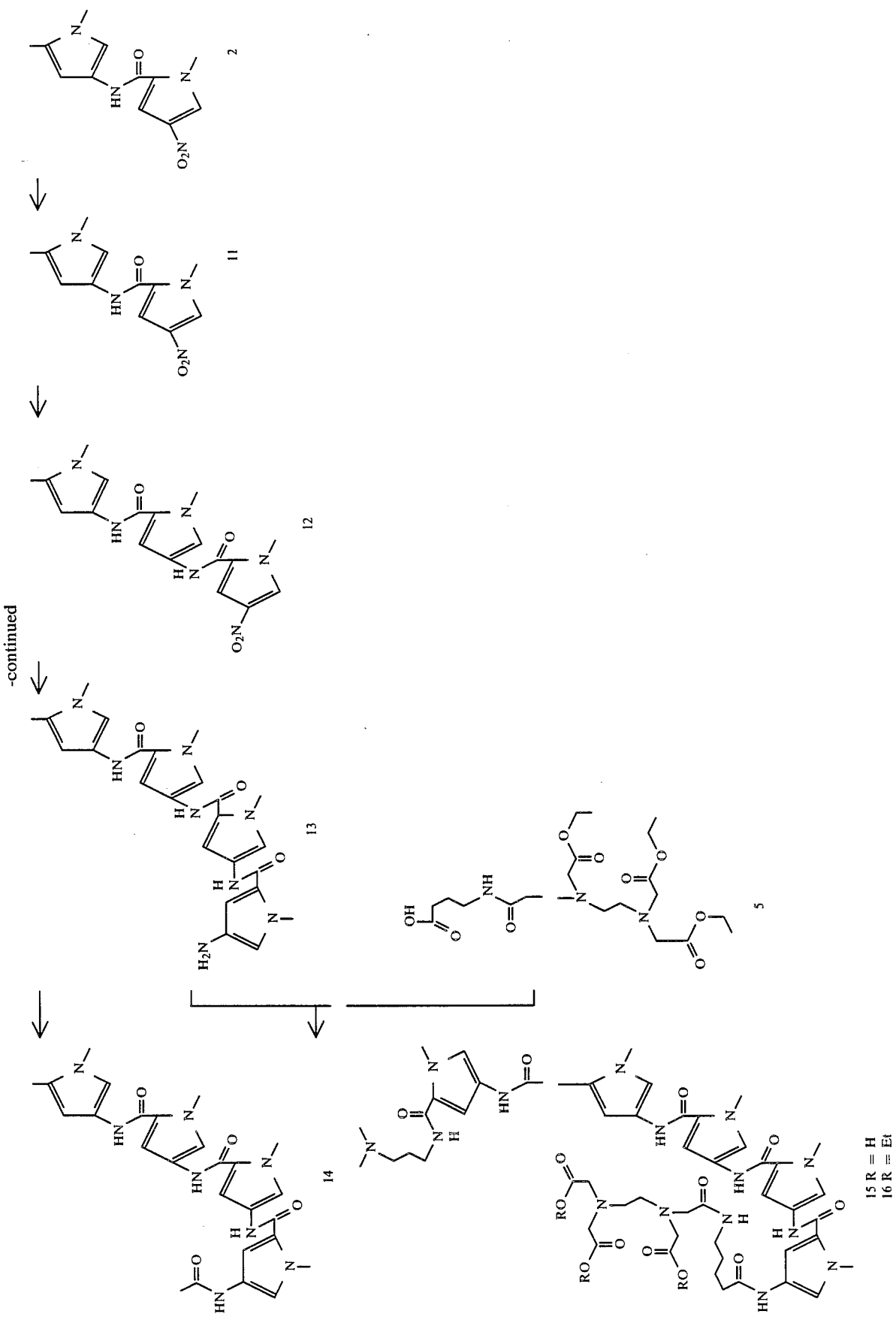

Fe(NH$_4$)$_2$(SO$_4$)$_2$·6H$_2$O was obtained from Baker and DTT from Calbiochem. Aqueous 5'-($\alpha^{32}$p)dATP triethylammonium salt, 3000 Ci/mmole, was from Amersham and aqueous 3'-($\gamma^{32}$p)dATP, 5000-9000 Ci/mmole, was from ICN. Nucleotide triphosphates were from Boehringer Mannheim. All enzymes were from New England Biolabs except bacterial alkaline phosphatase and T4 polynucleotide knase which were from BRL. Solutions of Fe(NH$_4$)$_2$(SO$_4$)$_2$, DTT and P5E were prepared freshly. P5E was characterized spectroscopically before use. DE and P5E were mixed immediately before use with Fe(II) at 1 mM concentrations and diluted approximately to yield P5E.Fe(II). DNA for this investigation was isolated from the bacterial plasmid pBR322 whose entire sequence is known, Sutcliffe, J. G. (1979) *Cold Spring Harbor Symp. Quant. Biol.*, 43, 77. Milligram quantities of the plasmid were grown in *Escherichia coli*, strain HB 101, and isolated by procedures similar to those of Tanaka and Weisblum. Calf thymus DNA (Sigma was sonicated, deproteinized and extensively dialyzed.

Cleavage Efficiency Assay

Each DNA cleaving reagent (DE.Fe(II) and P5E.Fe(II)) was allowed to equilibrate for 1 hour at 37° with supercoiled (form I) pBR322 DNA (10 μM in base pairs) in a buffer containing 40 mM Tris base and 5mM NaOAc at pH 7.9. The reaction was initiated by adding an aqueous solution of DTT (5 mM final concentration). Final concentrations are given in Table V. The cleavage reactions were allowed to run to completion (1.5 hours, 25°), quenched with 4 μl of a 50 mM Na$_2$EDTA, 10% ficol solution and electrophoresed on a 1% agarose gel at 120 V for 4 hours. Forms I, II, and III were analyzed by ethidium bromide staining, quantitated by densitometry and corrected for decreased stainability of form I DNA and for the presence of 1.5% form II in the original sample.

Double Strand Cleavage Assay

Linear pBR 322 plasmid DNA was obtained by digestion of superhelical plasmids with the restriction endonuclease Eco RI' followed by ethanol precipitation. P5E.Fe(II)/DTT reactions were carried out as described above. The final concentrations were: 0.5 μM P5E.Fe(II); 5 mM DTT; and 50 uM DNA. Reactions were analyzed by 1% agarose gel electrophoresis and ethidium bromide staining. The approximate P5E.Fe(II) cleavage sites were located by digestion of pBR 322 with several restriction enzymes followed by P5E.Fe(II) (0.5 μM) cleavage. Changes in the lengths of the resulting DNA fragments could be correlated with cleavage sites. Mapping restriction enzymes used were Eco RI, Sal I, Nde I, Ava I, Hind II+Ava I, Taq I, and Rsa I.

Preparation of Specific Labeled DNA Fragments

Superhelical pBR 322 plasmid DNA was digested with the restriction endonuclease Eco RI and then labeled at the 3 end with ($\alpha$-$^{32}$P)dATP using the Klenow fragment of DNA polymerase I. A second enzymatic digest with the restriction endonuclease Rsa I yielded two end labeled fragments, 167 and 517 nucleotides in length. These were isolated by gel electrophoresis on a 5% polyacrylamide, 1:30 crosslinked, 2 mm thick gel. Isolation of the two fragments from the gel and subsequent procedures were similar to those of Maxam and Gilbert. Cleavage of pBR 322 with Eco RI, and successive treatment with bacterial alkaline phosphatase, ($\gamma$-$^{32}$P)ATP and T4 polynucleotide knase, followed by restriction with Rsa I yielded the 517 and 167 bp DNA fragments labeled with $^{32}$P at the 5 end.

High Resolution Denaturing Gel

The cleavage reactions were run as described above with >600 cpm of $^{32}$P end labeled restriction fragments made up to a total DNA concentration of 100 μM (bp) with sonicated calf thymus DNA. Final concentrations are: 1.2 μM P5E.Fe(II) and 1 mM DTT. The reactions were run at 25° for 1 hour, terminated by freezing (−78° C.), lyophilized and suspended in 4 μl of a pH 8.2 100 mM Tris-Borate, 50% formamide solution. These samples were heat denatured and loaded on a 0.4 mm thick, 40 cm long, 8% polyacrylamide, 1:20 crosslinked, 50% urea gel and electrophoresed at 1500 V. Autoradiography of the gels was carried out at −50° on Kodak, X-Omat AR film and the autoradiograms were scanned at 485 nm on a Cary 219 spectrophotometer. The relative peak area for each site was equated to the relative cleavage efficiency.

RESULTS

Cleavage Efficiency

The DNA cleavage efficiency of P5E.Fe(II) was followed by monitoring the conversion of supercoiled pBR 322 plasmid DNA (form I) to open circular (form II) and linear forms (form III). Unlike DE.Fe(II), P5E.Fe(II) requires equilibration (37°, 1 hour) with the DNA before initiation of cleavage with DTT for optimum efficiency. In the presence of O$_2$ and DTT (5 mM), P5E.Fe(II) at 0.01 μM concentration cleaves DNA (10 uM base pairs) almost two orders of magnitude more efficiently than distamycin-EDTA.Fe(II) (DE.Fe(II)). Importantly, P5E.Fe(II) at 0.01 nM concentration in the presence of 5 mM DTT cleaves form I pBR 322 DNA at 0.22 μM plasmid (1 mM bp) to 40% form II DNA. (Table V). Assuming the conversion of form I to form II represents a minimum of one strand scission, this result corresponds to a minimum of nine single strand cleavage events per P5E.Fe(II) molecule.

TABLE V

Cleavage of pBR 322 Plasmid DNA
(10 μM bp) in the Presence of 5 mM DTT[a,b]

| Reagent | conc, M | Form % I | II | III |
|---|---|---|---|---|
| EDTA.Fe(II) | 10$^{-6}$ | 96 | 4 | 0 |
| DE.Fe(II) | 10$^{-6}$ | 32 | 68 | 0 |
| P5E.Fe(II) | 10$^{-6}$ | 3 | 59 | 38 |
| P5E.Fe(II) | 10$^{-7}$ | 48 | 47 | 5 |
| P5E.Fe(II)[c] | 10$^{-7}$ | 60 | 40 | 0 |

[a]All reactions were run to completion.
[b]P5E was preequilibrated at 37° for 1 hour.
[c]DNA at 1 mM bp.

Double Strand Cleavage

The sequence specific double strand cleavage of DNA by P5E.Fe(II)/DTT was examined on linear pBR 322 plasmid DNA, 4362 base pairs in length, obtained by cleavage of supercoiled pBR 322 plasmid with Eco RI. P5E.Fe(II) (0.5 to 1.0 μM) was allowed to equilibrate at 37° for 1 hour with the linear plasmid DNA (50 μM) followed by addition of DTT (5 mM) to initiate reaction. After 1 hour the reaction mixture was analyzed by agarose gel electrophoresis. The major observarion is that P5E.Fe(II) (P5E/bp=0.01) cleaves linear pBR 322 DNA into discrete DNA fragments. Restriction mapping indicates major double strand cleavage sites are centered at approximately 4.3, 4.2, 3.3 and 3.2 kilobases (kb) with minor sites at 2.6, 2.4, 2.0 and 1.8 kb. At higher P5E concentrations ($\geq 1.0$ $\mu$M) the specificity of the cleavage reaction is diminished.

DNA Cleavage Pattern Analyses

The cleavage sites of P5E.Fe(II) can be resolved in greater detail by analysis of the DNA cleavage patterns using $^{32}$P end labeled restriction fragments and high resolution denaturing gel electrophoresis. A 517 base pair Rsa I-Eco RI restriction fragment from pBR 322, nucleotides 3848-4362, containing two major P5E.-Fe(II) cleavage sites (4.3 and 4.2 kb) was chosen for study. The Eco RI site was labeled separately with $^{32}$P on the 5' and 3' ends. The resulting DNA fragments were allowed to react with P5E.Fe(II) (P5E/base pair=0.012) for 1 hour, then stopped by freezing, lyophilized and suspended in formamide buffer. The $^{32}$P end labeled DNA cleavage products were analyzed by Maxam-Gilbert sequencing gel methods. A histogram of the DNA cleavage patterns obtained from densitometric analysis of the autoradiogram reveals major cleavage sites covering 3-5 base pairs contiguous to a six base pair region of A+T rich DNA (base pairs 4323-4324). The cleavage sites flanking this region are of unequal intensity with major cleavage on the adenine side of a six base pair 5'-TTTTTA-3' sequence. Minor cleavage sites flank the sequence 5'-TAATAAT-3', located at base pairs 4300-4306. The cleavage patterns produced on opposite strands are asymmetric, shifted to the 3' side of each DNA strand.

EXAMPLE VI

Bis(EDTA distamycin) and EDTA-(bisdistamycin) were prepared as follows:

Bisdistamycin 19—A solution of 0.25 g (0.5 mmol) nitro amine 2 in 10 mL dimethylformamide was hydrogenated over 2000 mg of 5% palladium on charcoal at 50 psi hydrogen on a Parr rocker for 12 hours. The mixture was filtered through Celite affording the crude amine 3. The celite was washed with 10 ml DMF. To this solution was added with stirring 0.09 g (0.28 mmol) of di-N-hydroxysuccinimide-heptane dicarbosylic acid which was prepared as follows. To a solution of 5t (31.0 mmol) pimelic acid and 7.9 g (68 mmol) N-hydroxysuccinimide was added with stirring 14 g (68 mmol) of dicyclohexylcarbodiimide in 20 ml dioxane The solution was stirred for 12 hours, filtered, concentrated and chromatographed on silica gel with 25% ethyl acetate in dichloromethane.

After 12 hours DMF was removed from the bisdistamycin under high vacuum at 35° C., the residue was triturated three times with ether and purified by flash chromatography on silica gel with 5% concentrated aqueous ammonia (33%) in methanol affording 0.30 g (70%) BD: IR (KBr) 3280, 2940, 1640, 1580, 1530, 1460, 1430, 1400, 1250, 1200 cm$^{-1}$; NMR (DMSO−d$_6$) $\delta$1.3 (m,2H), 1.5 (m,8H), 2.1 (s,12H), 2.2 (m,8H), 3.15 (m,4H), 3.8 (s,3H), 3.85 (s,3H), 3.77 (s,3H.:, 6.8 (d,2H,J=1.65 Hz), 6.85 (d,2H,J=1.5 Hz), 7.04 (d,2H,J=1.5 Hz), 7.15 (m,4H), 7.25 (d,2H,J=1.5 Hz), 8.05 (t,2H,J=6 Hz), 9.8 (s,2H), 9.9 (s,4H), UV (EtOH) 305 nm (70,000)103 230 nm, m/e 1061 (M+).

Bis(EDTA-triethylester distamycin BED.Et3—A solution of 0.25 g (0.23 mmol) nitro-EDTA triethylester 10 in 10 ml DMF was hydrogenated over 200 mg of 5% Pd/C at 50 psi hydrogen on a Parr rocker for 12 hours. The mixture was filtered through celite and the celite was washed with 10 ml DMF. To this solution was added with stirring 0.041 g (0.1 mmol) di-N-hydroxysuccinimide heptane dicarboxylic acid. After 12 hours, DMF was removed under high vacuum at 35° C., the residue was triturated three times with ether and purified by flash chromatography on silica gel with 35% concentrated aqueous ammonia in methanol to yield 0.2 g (80%) BED.Et3 31: IR (KBr) 3290, 2940, 1735, 1660, 1640, 1580, 1530, 1460, 1430, 1255, 1200 cm$^{-1}$; NMR (DMSO−d$_6$) $\delta$1.18 (t, 18H,J=8 Hz), 1.3 (m,2H), 1.6 (m,12H), 2.13 (s,6H), 2.25 (t,4H,J=7 Hz), 2.3 (m,8H),2.68 (m,4H), 2.73 (m,4H), 3.13 (m,4H), 3.18 (m,4H), 3.2 (m,4H), 3.5 (m,4H), 3.59 (m,8H), 3.8 (s,6H), 3.86 (s,6H), 3.97 (s,6H), 4.05 (m,12H), 6.82 (d,2H,J=1.5 Hz), 6.86 (d,2H,J=1.5 Hz), 7.05 (d,2H,J=1.5 Hz':, 7.18 (d,2H,J=1.5 Hz), 7.20 (d,2H,J=1.5 Hz), 7.23 (d,2H,H=1.5 Hz), 7.96 (s,2), 8.02 (s,2H), 9.77 (s,2H), 9.88 (s,2H), 10.0 (s,2H); UV (H$_2$O) 306 nm, 235; m/e 1864 (M+).

Bis(EDTA-distamycin) BED 17—To a solution of 0.25 g (0.14 mmol) BED.Et3 in 5 mL ethanol was added with stirring 5 mL of 0.25M aqueous lithium hydroxide. The resulting solution was stirred for 12 hours and acidified to pH4 with 10% aqueous hydrochloric acid. The solvent was removed under high vacuum at 35° C., the residue was triturated three times with ether and purified by flash chromatography on silica gel with 5% concentrated aqueous ammonia (33%) in methanol. Final purification was carried out by loading the product dissolved in water onto an amberlite XAD-2 column and washing with 1 1 3% aqueous Na$_2$EDTA and 2 1 doubly distilled water. Elution with methanol afforded 0.15 g (62%) BED 17; (KBr): 3300, 2940, 1740, 1660, 1640, 1570, 1540, 1470, 1440, 1410, 1260 cm$^{-1}$; NMR (DMSO−d$_6$): 1.25 (m,2H), 1.65 (m,4H), 1.9 (m,8H), 2.3 (t,4H,J=7 Hz), 2.7 (s,6H), 3.1 (m,8H), 3.25 (m,4H), 3.3 (m,4H), 3.4 (m,4H), 3.45 (m,4H), 3.8 (3s,18H), 3.94 (s,8H), 4.0 (s,4H). 4.1 (s,4H), 6.9 (s,4H), 7.0 (d,2H,J=1.5 Hz), 7.17 (d,2H,J=1.5 HZ), 7.20 (d,2H,J=1.5 Hz), 7.23 (d,2H,J=1.5 Hz), 8.2 (s,2H), 8.83 (s,2H), 9.95 (3s,6H); UV (H$_2$O) 306 (70,000)$^{103}$ 235 nm; m/e 1696 (M+).

Dimethylamino tri-N-methylpyrrole heptanoic acid 21—A solution of 0.5 g (1 mmol) nitro amine 2 in 10 m] dimethylformamide was hydrogenated over 200 mg pd/C at 50 psi hydrogen on a Parr rocker for 12 hours. The mixture was filtered through celite and the celite was washed with 10 ml DMF. The combined solution was added with stirring to 2 mmol heptane dicarboxylic acid monoimidazolide in 10 ml DMF. Heptane dicarboxylic acid monoimidazolide was synthesized by adding with stirring 0.4 g (2 mmol) acyldiimidazole to 1.6 g (10 mmol) heptane dicarboxylic acid in 10 ml DMF and stirring an additional 1 hour. After 12 hours, 10 ml H$_2$O was added to the reaction mixture, solvent was removed under vacuum at 35° C., the residue was triturated three times with ether and purified by flash chromatography on silica gel with 2% concentrated aqueous ammonica in methanol to afford 0.5 g (5%) amino acid 21; IR (KBr) 3300, 2950, 1660, 1640, 1570, 1530, 1460, 430, 1400, 1260, 1200 cm$^{-1}$; NMR (DMSO−d$_6$) $\delta$1.3 (m,2H), 1.4-1.6 (m,3H), 2.15 (s,6H), 2.25 (m,6H), 3.2 (m,2H), 3.75 (s,3H), 3.8 (s,3H), 3.83 (s,3H), 6.85 (d,1H,J=1.5 Hz), 6.90 (d,1H,J=1.5 Hz), 7.05 (d,1H,J=1.5 Hz), 7.15 (m,2H), 7.2 (d,1H,J=1.5 Hz), 8.1

(t,1H,J=6 Hz), 9.8 (s,1H), 9.9 (s,1H), 9.93) (s,1H); UV (H$_2$O) 302 nm, 238 nm; m/e 611 (M+).

EDTA bisdistamycin triethylester E(Et$_3$)BD—0.37 g (0.41 mmol) nitro EDTA triester 10 in 15 ml DMF was hydrogenated over 200 mg Pd/C at 50 psi hydrogen on a Parr rocker for 12 hours. This solution was filtered through celite and the celite was washed with 10 ml DFM to afford the crude amine. To 0.25 g (0.41 mmol) amino acid 21 in 15 ml dimethylformamide was added with stirring 0.09 g (0.49 mmol) acyldiimidazole. After 1 hour the crude amine solution was added to the imidazolide with stirring and the resulting solution stirred for 12 hours at 25° C. The DMF was removed uhder vacuum at 35° C., the resulting residue triturated three times with ether and purified by flash chromatography on silica gel with 4.5% concentrated aqueous ammonia in methanol to afford 0.45 g (73%) EBD triethyl ester: IR (KBr) 3290, 2950, 1740, 1670, 1640, 1590, 1560, 1470, 1440, 1410, 1260, 1210 cm$^{-1}$; NMR (DMSO—d$_6$) δ1.2 (t,9H,J=7 Hz), 1.3 (m,2H), 1.6 (m,10 H), 2.15 (s,9H), 2.3 (t,4H,J=7 Hz), 2.35 (m,6H), 2.7 (m,4H), 3.15 (m,2H), 3.2 (m,6H), 3.5 (s,4H), 4.6 (s,2H), 3.85 (s,m3H), 3.9 (s,3H), 3.92 (s,3H), 6.85 (s,1H), 6.87 (s,1H), 6.9 (s,2H) 7.06 (s,2H), 7.15 (s,2H), 7.17 (s,2H), 7.23 (s,2H), 7.95 (t,1H,J=7 Hz), 8.0 (t,1H,J=7 Hz), 8.05 (t,1H,J=7 Hz), 9.85 (s,2H), 9.95 (s,2H), 9.96 (s,2H); UV (EtOH) 303 nm, 235 nm; m/e 1463 (M+).

EDTA-bis distamycin-EBD 18—To a solution of 0.2 g (0.14 mmol) triester 33 in 5 ml ethanol was added with stirring 5 ml of 0.25M aqueous lithium hydroxide. The resulting solution was stirred for 12 hours and acidified to pH 4 with 10% hydrochloric acid. The solvent was removed under high vacuum at 35° C. and the residue purified by flash chromatography on silica gel with 5% concentrated ammonia hydroxide in methanol. Final purification was carried out by loading the product, dissolved in distilled H$_2$O onto a nonionic amberlite XAD-2 column and washing, with 1 l 3% aqueous Na$_2$EDTA and 2l doubly distilled water. Elution with methanol afforded 0.1 g (52%) EBD: IR (KBr) 3310, 2950, 1730, 1650, 1640, 1560, 1530, 1460, 1430, 1400, 1260, 1200 cm$^{-1}$; NMR (DMSO—d$_6$) 1.3 (m,2H), 1.65 (m,4H), 1.9 (m,6H), 2.25 (t,4H,J=7 Hz), 2.75 (s,9H), 3.05 (m,6H), 3.2 (m,6H), 3.4 (m,4H), 3.9 (3s, 9H), 3.95 (s,4H), 4.0 (s,2H), 4.1 (s,2H), 6.9 (s,4H), 7.03 (d,2H,J=1.5 Hz), 7.15 (d,2H,J=1.5 Hz), 8.3 (s,2H), 8.9 (t,1H,J=7 Hz), 9.9 (3s,6H); UV (H$_2$O) 303 (70,000)$^{103}$, 235 nm; m/e 1396 (M+).

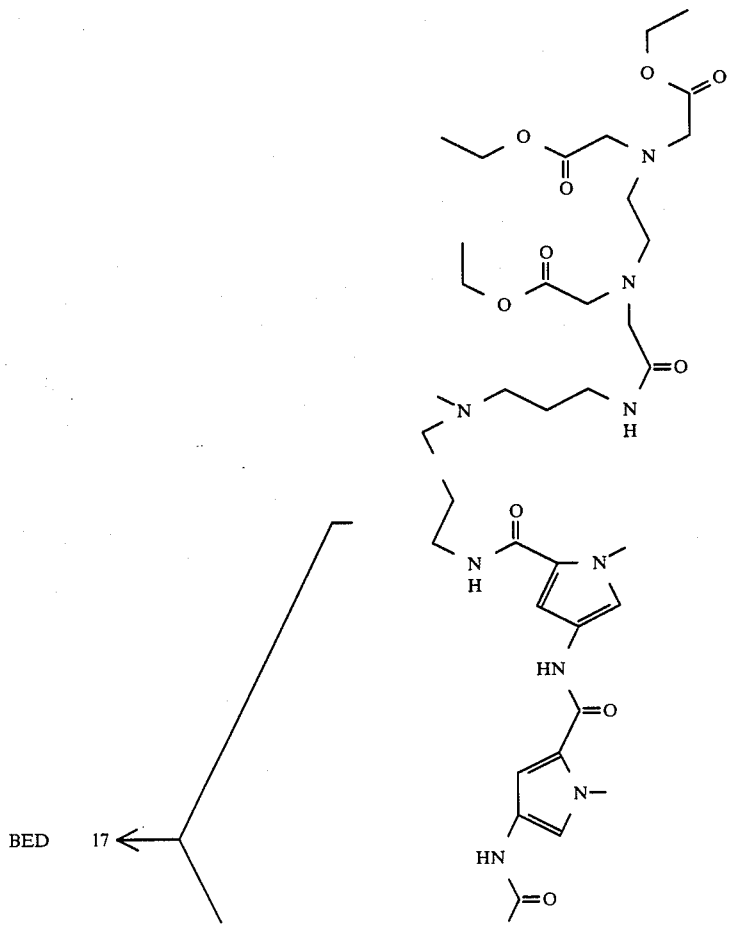

BED  17

-continued
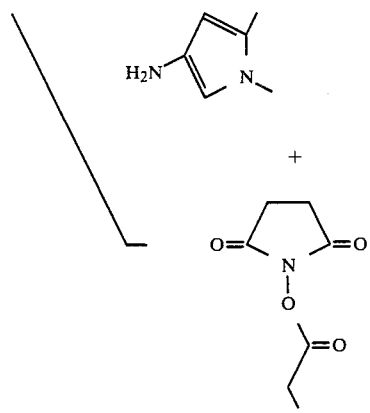
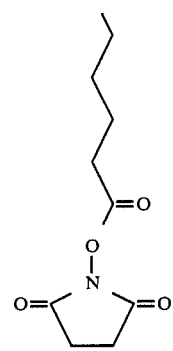
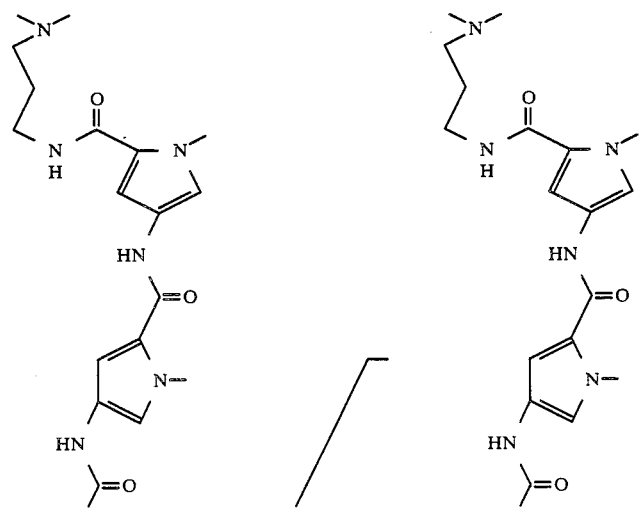

-continued
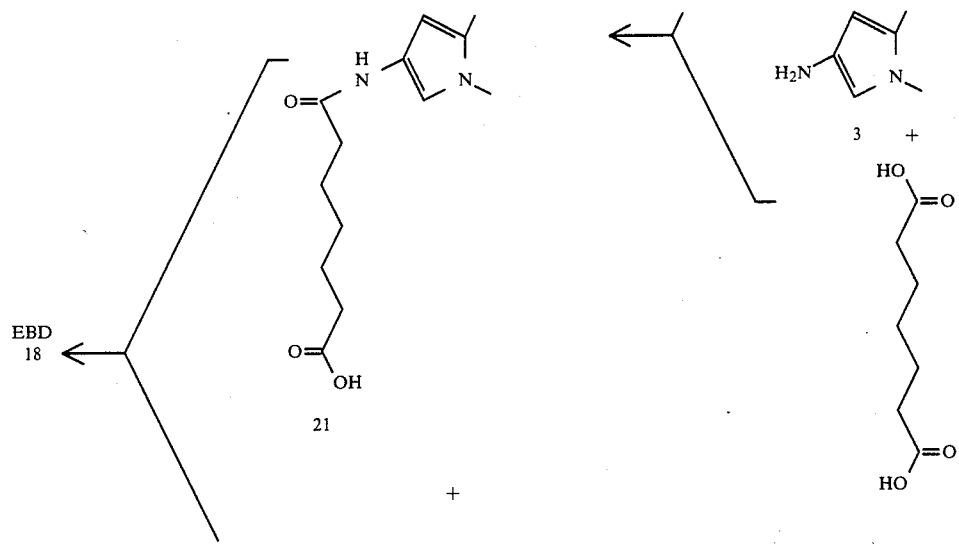
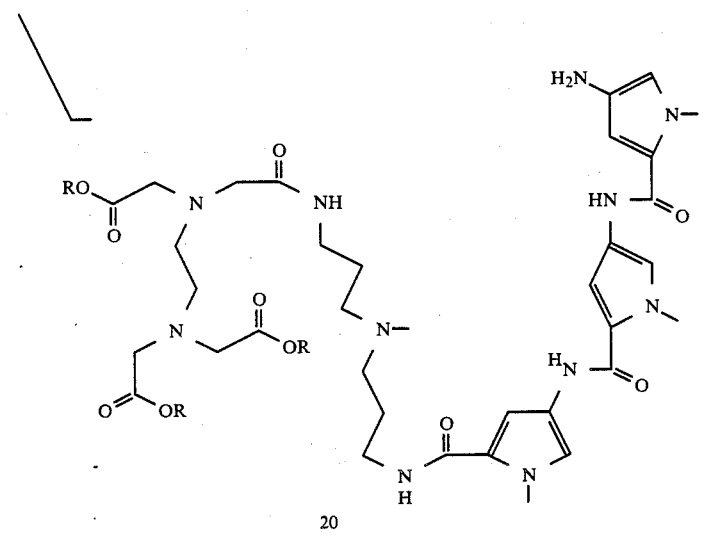
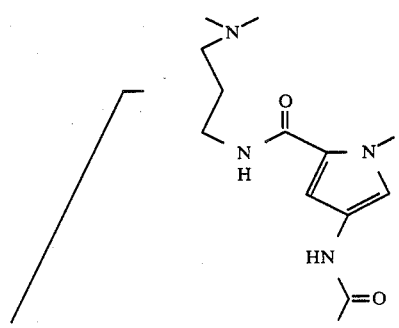

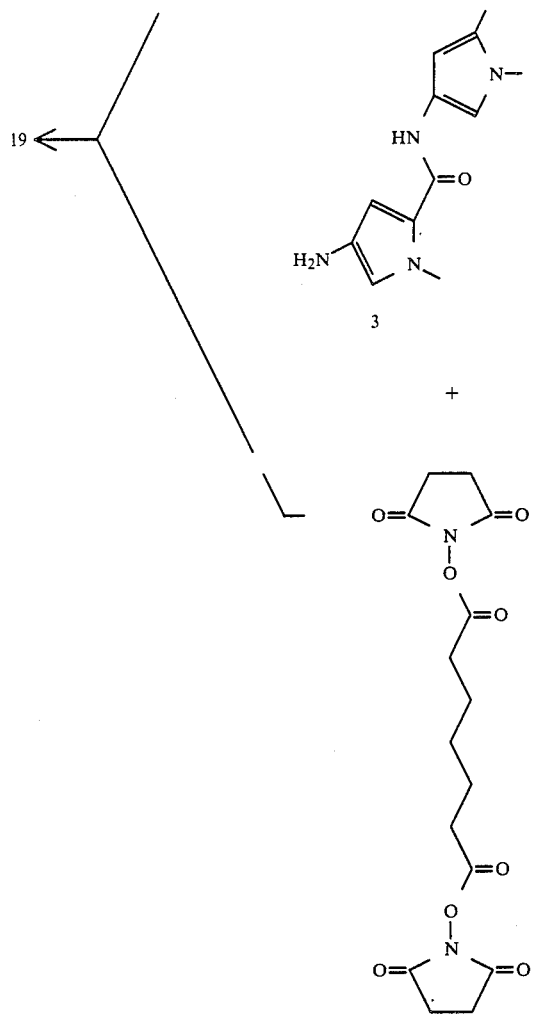

BED and EBD were converted to BED.Fe(II) and EBD.Fe(II), respectively by mixing with Fe(NH$_4$)$_2$(SO$_4$)$_2$ and DTT at 1 mM concentrations.

The DNA cleavage efficiency of BED.Fe(II) and EBD.Fe(II) was followed by monitoring the conversion of supercoiled pBR 322 plasmid DNA (form I) to open circular (form II) and linear forms (form III). One single strand scission converts from form I to form II. In the presence of O$_2$ and DTT, nanomolar concentrations of BED.Fe(II) and EBD.Fe(II) cleave DNA (10 μM base pair), almost three orders of magnitude lower concentration than required for efficient ED.Fe(II) cleavage. (Table VI) BED.Fe(II) affords a higher proportion of form III linear DNA than EBD.Fe(II) at 10$^{-7}$ and 10$^{-8}$ M suggesting that BED.Fe(II) may cleave on opposite strands in a single binding event.

TABLE VI

| | Cleavage of pBR 322 Plasmid | | | |
| | | Form % | | |
| Reagent | conc. μM | I | II | III |
| --- | --- | --- | --- | --- |
| ED.Fe(II) | 10.0 | 0 | 80 | 20 |
| ED.Fe(II) | 1.0 | 10 | 85 | 5 |
| EBD.Fe(II) | 0.010 | 0 | 82 | 18 |
| EBD.Fe(II) | 0.001 | 43 | 48 | 9 |
| BED.Fe(II) | 0.010 | 9 | 55 | 36 |
| BED.FE(II) | 0.001 | 48 | 42 | 10 |

Form I pBR 322 (10 μM bp), reagent, buffer (40 mM Tris base, 5 mM NaOAc, pH 7.9) and DTT (5 mM) were allowed to react at 25° C. for one hour and quenched. In all cases reactions were carried to completion. Forms I, II, and III were analyzed by agarose gel electrophoresis and quantitated by densitometry after ethidium bromide staining.

Sequence specific double strand cleavage of DNA by BED.Fe(II) and EBD.Fe(II) was examined on linear pBR 322 plasmid DNA (4362 bp). (Linear pBR322 was obtained by digestion of supercoiled pBR 322 with Eco RI and Sal I restriction enzymes, respectively). BED.Fe(II) or EBD.Fe(II) (0.25 μM or 0.06 μM) was equilibrated with linear pBR 322 DNA (50 μMbp) for 30 min (37° C.), followed by addition of DTT (5 mM). After one hour, the reaction was quenched and analyzed by agarose gel electrophoresis. Both BED.Fe(II) and EBD.Fe(II) (0.06 μM) cleave linear pBR 322 into discrete fragments. Restriction mapping indicates the major cleavage sites are at approximately 3.3 and 4.2 kilobases, (The cleavage sites were located by initially linearizing pBR-322 with Eco RI, Sal I, Nde I, Ava I, Eco RI+Sal I, Hind II+Ava I, Taq I, and Rsa I restriction enzymes, followed by BED.Fe(II) or EBD.Fe(II) cleavage. Changes in the lengths of the resulting DNA fragments could be correlated with cleavage sites.) regions of pBR 322 with high poly (dA).poly(dT) content. Cleavage specificity diminishes at higher concentrations of BED.Fe(II) and EBD.Fe(II), presumably due to cleavage at sites of diminished binding affinity.

The sequence and size of BED.Fe(II)/EBD.Fe(II) recognition sites can be resolved by analysis of DNA cleavage patterns using $^{32}P$ end-labeled restriction fragments and high resolution denaturing polyacrylamide gel electrophoresis. A 517 base pair Rsa I/Eco RI restriction fragment (3848–4362 bp) from pBR 322 was labeled separately with $^{32}P$ (Eco RI site) on the 5' and 3' ends. The resulting DNA fragments were allowed to react with BED.Fe(II) or EBD.Fe(II) at dimer/bp ratios of 0.01 in the presence of DTT (1 mM) for one hour (The reactions were run with >600 cpm of $^{32}P$ end labeled restriction fragments made up to a total DNA concentration of 100 μM (bp) with sonicated calf thymus DNA. The reactions were run at 25° C. for 1 hour and terminated by freezing, lyophilized and suspended in 4 vl of a pH 8.3 100 mM Tris-Borate, 50% formamide solution. These solutions were heat denatured and loaded on a 0.4 mm thick, 40 cm long, 8% polyacrylamide, 1:20 crosslinked, 50% urea gel and electrophoresed at 1500 V. Autoradiography of the gels was carried out at −50° C. on Kodak, X-Omat AR film and the autoradiograms scanned at 485 nm. The relative peak area for each site was equated to the relative cleavage efficiency.) and analyzed by gel electrophoresis. A histogram of the DNA cleavage patterns obtained from densitometric analysis of the autoradiograms reveals a major cleavage site contiguous to the eight base pair sequence 5'-TTTTTATA-3' and a minor site contiguous to the five base pair sequence 5'-AATAA-3'.

The multiple asymmetric cleavage patterns on opposite DNA strands presumably result from a diffusible oxidizing species, such as hydroxyl radical, generated in the minor groove of a right-handed DNA double helix. (The DNA cleavage products are consistent with oxidative cleavage of the deoxyribose ring affording a 5' phosphate DNA terminus and approximately equal proportions of 3' phosphate and 3' phosphoglycolate termini. Like the tripeptides DE and ED, the dimer EBD can apparently assume two orientations on the DNA. The eight base pair 5'-TTTTTATA-3' and the five base pair 5'-AATAA-3' binding sites suggest that the hydrocarbon tether allows both dimeric and monomeric binding modes. Changes in linker length and/or flexibility might lead to exclusive dimeric binding.

In conclusion, we have found that the dimer of a sequence specific single strand DNA cleaving molecule results in molecules capable of double strand cleaving plasmid pBR 322 into discrete fragments. This work illustrates a general strategy for the design of double strand DNA cleaving molecules with defined target sequences and binding site sizes.

Having fully described the invention it is intended that it be limited solely by the lawful scope of the appended claims.

We claim:

1. The compounds having the general formula:

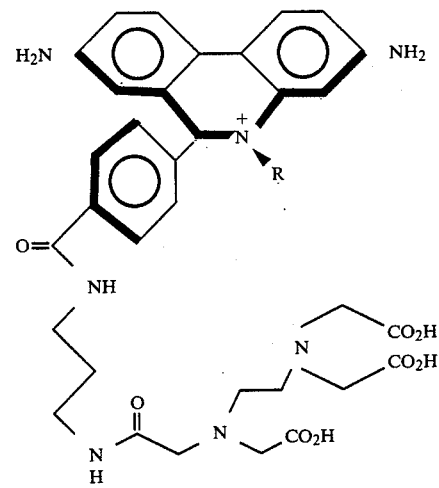

wherein R is methyl or ethyl.

2. The composition of claim 1 wherein the compound is methidiumpropyl ethylenediamine tetraacetic acid.

3. The composition of claim 1 wherein the compound is ethidiumpropyl ethylenediamine tetraacetic acid.

* * * * *